US012003869B2

(12) United States Patent
Breisacher et al.

(10) Patent No.: US 12,003,869 B2
(45) Date of Patent: Jun. 4, 2024

(54) SYSTEMS AND METHODS FOR TRACKING OBJECTS

(71) Applicant: MAKO Surgical Corp., Weston, FL (US)

(72) Inventors: Jochen Breisacher, Teningen (DE); David Hofmann, Freiburg (DE); Emeric Umbdenstock, Freiburg (DE); Jonathan Morgan, Biscayne Park, FL (US); Paul Hoekstra, Kalamazoo, MI (US)

(73) Assignee: MAKO Surgical Corp., Weston, FL (US)

( * ) Notice: Subject to any disclaimer, the term of this patent is extended or adjusted under 35 U.S.C. 154(b) by 0 days.

(21) Appl. No.: 18/213,360

(22) Filed: Jun. 23, 2023

(65) Prior Publication Data

US 2023/0329803 A1 Oct. 19, 2023

Related U.S. Application Data

(63) Continuation of application No. 17/972,625, filed on Oct. 25, 2022, now Pat. No. 11,723,726, which is a
(Continued)

(51) Int. Cl.
*H04N 25/44* (2023.01)
*A61B 34/20* (2016.01)
(Continued)

(52) U.S. Cl.
CPC ............ *H04N 25/44* (2023.01); *A61B 34/20* (2016.02); *H04N 23/60* (2023.01); *H04N 23/61* (2023.01);
(Continued)

(58) Field of Classification Search
CPC ...... H04N 25/40; H04N 25/44; H04N 25/443; A61B 34/20; A61B 2034/2046;
(Continued)

(56) References Cited

U.S. PATENT DOCUMENTS 5,295,483 A 3/1994 Nowacki et al.
5,817,105 A 10/1998 Van Der Brug
(Continued)

FOREIGN PATENT DOCUMENTS

WO 2016041050 A1 3/2016
WO 2017054817 A1 4/2017
(Continued)

OTHER PUBLICATIONS

English language abstract and machine-assisted English translation for WO 2017/054817 extracted from espacenet.com database on Jul. 15, 2019, 29 pages.
(Continued)

*Primary Examiner* — David N Werner
(74) *Attorney, Agent, or Firm* — Howard & Howard Attorneys PLLC

(57) ABSTRACT

Systems and methods to track an object within an operating room with a camera unit. The camera unit includes a first optical sensor with sensing elements to sense light in a near-infrared spectrum and a second optical sensor to sense light in a visible light spectrum. A controller is in communication with the first and second optical sensors. The controller obtains, from the second optical sensor, data related to the object within the operating room. The controller modifies control of the sensing elements of the first optical sensor based on the data of the object obtained by the second optical sensor.

20 Claims, 10 Drawing Sheets

Related U.S. Application Data continuation of application No. 17/317,191, filed on May 11, 2021, now Pat. No. 11,510,740, which is a continuation of application No. 16/441,645, filed on Jun. 14, 2019, now Pat. No. 11,007,018.

(60) Provisional application No. 62/685,470, filed on Jun. 15, 2018.

(51) Int. Cl.
*H04N 23/60* (2023.01)
*H04N 23/61* (2023.01)
*H04N 25/40* (2023.01)
*H04N 25/443* (2023.01)
*A61B 34/00* (2016.01)
*H04N 23/695* (2023.01)
*H04N 25/42* (2023.01)

(52) U.S. Cl.
CPC ......... *H04N 25/40* (2023.01); *H04N 25/443* (2023.01); *A61B 2034/2046* (2016.02); *A61B 2034/2055* (2016.02); *A61B 2034/2057* (2016.02); *A61B 2034/2065* (2016.02); *A61B 34/70* (2016.02); *H04N 23/695* (2023.01); *H04N 25/42* (2023.01)

(58) Field of Classification Search
CPC .... A61B 2034/2055; A61B 2034/2057; A61B 2034/2065
See application file for complete search history.

(56) References Cited

U.S. PATENT DOCUMENTS

| | | | |
|---|---|---|---|
| 6,141,104 A | 10/2000 | Schulz et al. | |
| 6,442,416 B1 | 8/2002 | Schultz | |
| 6,792,135 B1 | 9/2004 | Toyama | |
| 6,837,432 B2 | 1/2005 | Tsikos et al. | |
| 6,937,745 B2 | 8/2005 | Toyama | |
| 7,492,930 B2 | 2/2009 | Leitner et al. | |
| 7,725,162 B2 | 5/2010 | Malackowski et al. | |
| 8,155,479 B2 | 4/2012 | Hoffman et al. | |
| 8,181,878 B2 | 5/2012 | Nunnink et al. | |
| 8,244,495 B2 | 8/2012 | Goldbach et al. | |
| 8,743,222 B2 | 6/2014 | Hamalainen | |
| 8,792,963 B2 | 7/2014 | Zhao et al. | |
| 9,008,757 B2 | 4/2015 | Wu | |
| 9,119,655 B2 | 9/2015 | Bowling et al. | |
| 9,232,924 B2 | 1/2016 | Liu et al. | |
| 9,498,231 B2 | 11/2016 | Haider et al. | |
| 9,513,113 B2 | 12/2016 | Yang et al. | |
| 9,699,445 B2 | 7/2017 | Hoffman et al. | |
| 9,707,043 B2 | 7/2017 | Bozung | |
| 9,788,906 B2 | 10/2017 | Piron et al. | |
| 10,013,777 B2 | 7/2018 | Mariampillai et al. | |
| 10,038,888 B2 | 7/2018 | Hoffman et al. | |
| 10,178,368 B2 | 1/2019 | Zhao et al. | |
| 11,007,018 B2 | 5/2021 | Breisacher et al. | |
| 11,510,740 B2 | 11/2022 | Breisacher et al. | |
| 2005/0099601 A1 | 5/2005 | MacDougall et al. | |
| 2005/0105101 A1 | 5/2005 | Duling et al. | |
| 2007/0273766 A1* | 11/2007 | Wilson | G01S 3/7864 348/E3.018 |
| 2008/0107305 A1 | 5/2008 | Vanderkooy et al. | |
| 2008/0123820 A1 | 5/2008 | Kendrick et al. | |
| 2009/0248036 A1 | 10/2009 | Hoffman et al. | |
| 2010/0168763 A1 | 7/2010 | Zhao et al. | |
| 2010/0268067 A1 | 10/2010 | Razzaque et al. | |
| 2011/0235889 A1 | 9/2011 | Spahn | |
| 2012/0002084 A1 | 1/2012 | Weissman et al. | |
| 2013/0010087 A1 | 1/2013 | Nieten et al. | |
| 2013/0335417 A1 | 12/2013 | McQueston et al. | |
| 2014/0128881 A1 | 5/2014 | Tyc et al. | |
| 2014/0200621 A1 | 7/2014 | Malackowski et al. | |
| 2014/0340524 A1 | 11/2014 | Holz | |
| 2015/0141755 A1 | 5/2015 | Tesar | |
| 2015/0297313 A1 | 10/2015 | Reiter et al. | |
| 2015/0332465 A1 | 11/2015 | Schmidt et al. | |
| 2016/0275703 A1 | 9/2016 | Mariampillai et al. | |
| 2016/0335766 A1 | 11/2016 | Ambwani et al. | |
| 2017/0196641 A1 | 7/2017 | Jagga et al. | |
| 2017/0214858 A1* | 7/2017 | Keller | H04N 23/56 |
| 2017/0245946 A1 | 8/2017 | Tabandeh et al. | |
| 2017/0265949 A1 | 9/2017 | Crawford et al. | |
| 2017/0281283 A1 | 10/2017 | Siegler et al. | |
| 2017/0304007 A1 | 10/2017 | Piron et al. | |
| 2017/0325897 A1 | 11/2017 | Isaacs et al. | |
| 2017/0325898 A1 | 11/2017 | Isaacs et al. | |
| 2017/0340406 A1 | 11/2017 | Hendriks et al. | |
| 2018/0068441 A1 | 3/2018 | Yu et al. | |
| 2018/0106600 A1* | 4/2018 | Greenspan | G01B 11/002 |
| 2018/0140197 A1 | 5/2018 | Wang et al. | |
| 2018/0308263 A1 | 10/2018 | Mariampillai et al. | |
| 2019/0261931 A1 | 8/2019 | Ross | |
| 2019/0387149 A1 | 12/2019 | Breisacher et al. | |
| 2020/0078113 A1 | 3/2020 | Sawhney et al. | |
| 2020/0170718 A1 | 6/2020 | Peine | |
| 2020/0222123 A1 | 7/2020 | Handley et al. | |
| 2021/0052348 A1 | 2/2021 | Schwagli | |
| 2021/0259787 A1 | 8/2021 | Breisacher et al. | |
| 2023/0045799 A1 | 2/2023 | Breisacher et al. | |

FOREIGN PATENT DOCUMENTS

| | | |
|---|---|---|
| WO | 2017208186 A2 | 12/2017 |
| WO | 2018150336 A1 | 8/2018 |
| WO | 2018210422 A1 | 11/2018 |
| WO | 2019029934 A1 | 2/2019 |

OTHER PUBLICATIONS

Bouget, D. et al., Vision-Based and Marker-Less Surgery Tool Detection and Tracking: A Review of the Literature:, Med. Image Analysis, vol. 35, 2017, pp. 633-654.

* cited by examiner

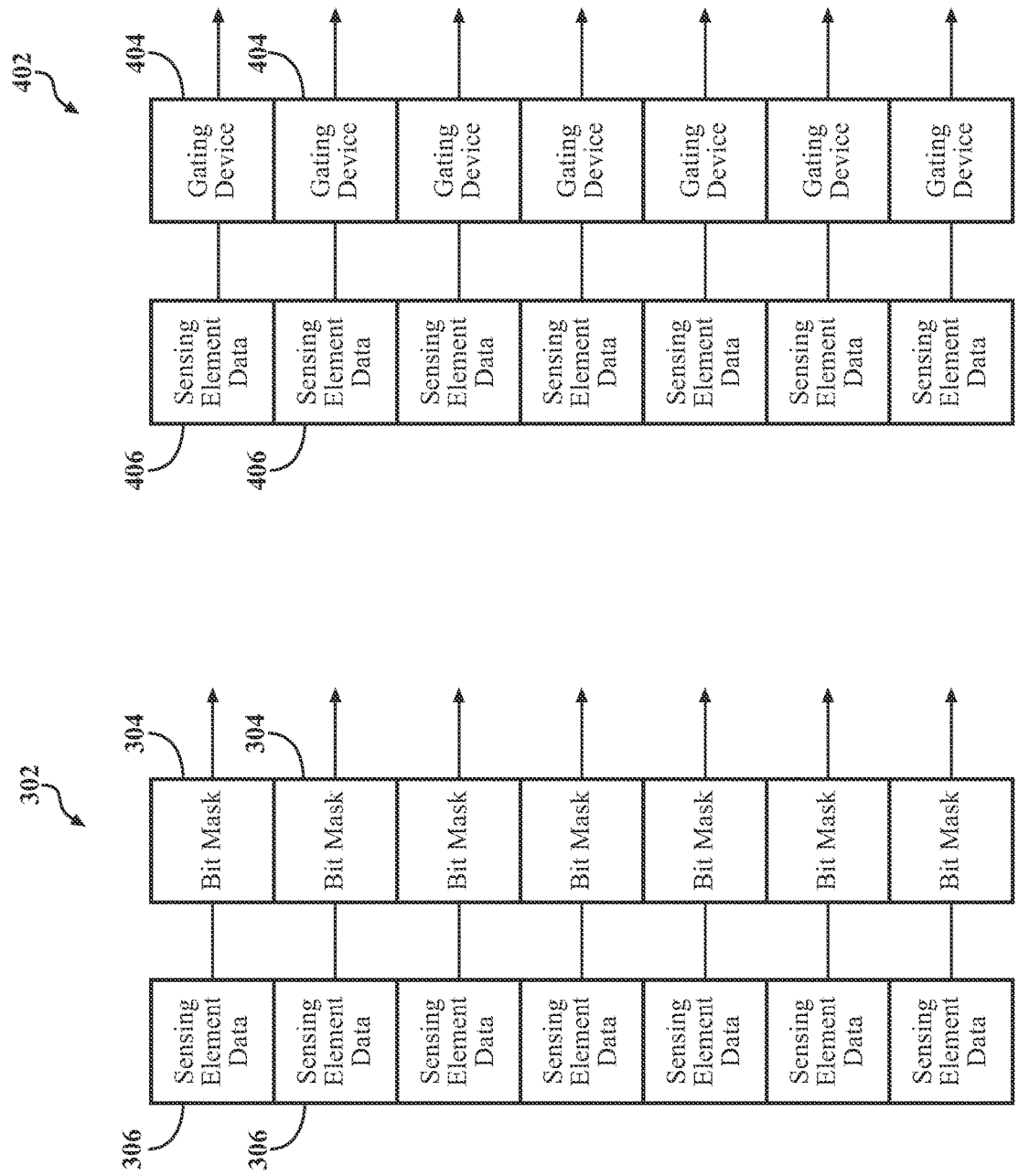

SYSTEMS AND METHODS FOR TRACKING OBJECTS

CROSS-REFERENCE TO RELATED APPLICATIONS

This application is a continuation of U.S. patent application Ser. No. 17/972,625, filed Oct. 25, 2022, which is a continuation of U.S. patent application Ser. No. 17/317,191, filed on May 11, 2021, now U.S. Pat. No. 11,510,740, which is a continuation of U.S. patent application Ser. No. 16/441,645, filed Jun. 14, 2019, now U.S. Pat. No. 11,007,018, which claims priority to and all advantages of U.S. Provisional Patent App. No. 62/685,470, filed on Jun. 15, 2018, the entire contents of each of the aforementioned applications being hereby incorporated by reference.

TECHNICAL FIELD

The present disclosure relates generally to systems and methods for tracking objects.

BACKGROUND

Navigation systems assist users in locating objects. For instance, navigation systems are used in industrial, aerospace, and medical applications. In the medical field, navigation systems assist surgeons in precisely placing surgical instruments relative to a patient's anatomy. Surgeries in which navigation systems are used include neurosurgery and orthopedic surgery. Typically, the instrument and the anatomy are tracked together with their relative movement shown on a display.

Navigation systems may employ light signals, sound waves, magnetic fields, RF signals, etc., in order to track the position and/or orientation of objects. Often the navigation system cooperates with tracking devices attached to the object being tracked. The navigation system includes a localizer to determine a position of the tracking devices, and ultimately to determine a position and/or orientation of the object. The navigation system monitors movement of the object via the tracking devices.

Frequently, localizers determine the position of tracked objects by sampling reflections or emissions of light from trackers attached to the tracked objects at a defined sampling rate. For example, some localizers sample light from the trackers at about 60 Hertz (Hz). Other localizers may sample light from the trackers up to about 335 Hz. Two-dimensional sensors employed by a localizer require processing a large volume of data. The localizer includes optical sensors, each sensor having an array of sensing elements and each sensing element having a range of values corresponding to the incident energy on the element. Processing an image from these values requires reading out the information from each element in sequence, that is—the readout processing cannot be parallelized. Sensors suitable for use in a localizer have a high number of elements with large ranges of values, so processing the sensor readout becomes a bottleneck and is a limiting factor in improving the sampling rate for tracking technologies. These sampling rates may be insufficient to detect rapid movement of the tracked objects adequately. Similarly, a low sampling rate may be insufficient to detect small movements of the tracked objects.

Increasing the sampling rate to address these shortcomings introduces its own challenges. For example, an increase in the sampling rate can substantially increase a processing workload for a processor that is tasked with analyzing the sampled signals to determine the presence and pose of the tracked objects. In some situations, the processor may not be able to keep up with the rate and number of sampled signals received from the trackers and may thus fail to detect changes in pose of the tracked objects. As described above, the readout from the sensor itself is a limiting factor in improving processing time as more data from the processor increases the workload of the processor.

The present disclosure addresses one or more of the above-described problems.

SUMMARY

According to a first aspect, a surgical navigation system is provided for tracking an object within an operating room, the surgical navigation system comprising: a camera unit comprising: a housing; a first optical sensor coupled to housing and comprising sensing elements adapted to sense light in a near-infrared spectrum; a second optical sensor coupled to the housing and being adapted to sense light in a visible light spectrum; and a controller in communication with the first and second optical sensors, and wherein the controller is configured to: obtain, from the second optical sensor, data related to the object within the operating room; and modify control of the sensing elements of the first optical sensor based on the data of the object obtained by the second optical sensor.

According to a second aspect, a method is provided of operating a surgical navigation system for tracking an object within an operating room, the surgical navigation system comprising a camera unit comprising a housing, a first optical sensor coupled to housing and comprising sensing elements adapted to sense light in a near-infrared spectrum, a second optical sensor coupled to the housing and being adapted to sense light in a visible light spectrum, and a controller in communication with the first and second optical sensors, the method comprising the controller performing the steps of: obtaining, from the second optical sensor, data related to the object within the operating room; and modifying control of the sensing elements of the first optical sensor based on the data of the object obtained by the second optical sensor.

According to a third aspect, a camera unit is provided for tracking an object within an operating room, the camera unit comprising: a first optical sensor comprising sensing elements adapted to sense light in a near-infrared spectrum; a second optical sensor adapted to sense light in a visible light spectrum; and a controller in communication with the first and second optical sensors, and wherein the controller is configured to: obtain, from the second optical sensor, data related to the object within the operating room; and modify control of the sensing elements of the first optical sensor based on the data of the object obtained by the second optical sensor.

BRIEF DESCRIPTION OF THE DRAWINGS

Advantages of the present disclosure will be readily appreciated as the same becomes better understood by reference to the following detailed description when considered in connection with the accompanying drawings wherein:

FIG. 11 is a block diagram of a bit mask array that may be used to select a subset of sensor elements used by the navigation system.

FIG. 12 is a block diagram of an array of gating devices that may be used to select a subset of sensing elements used by the navigation system.

DETAILED DESCRIPTION

Figure 1:
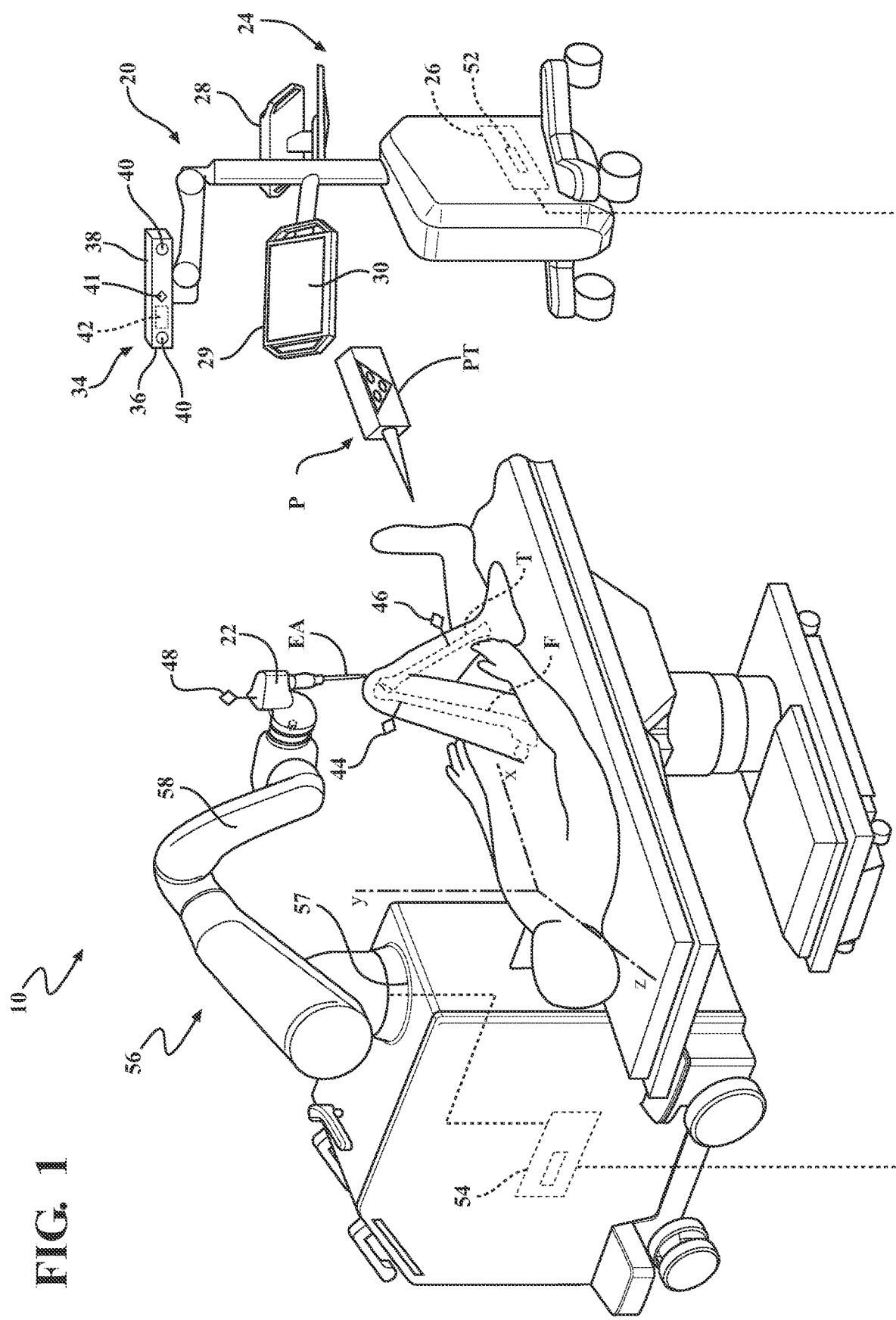
FIG. 1 is a perspective view of a navigation system being used in conjunction with a robotic system.

Referring to FIG. 1, a surgical system 10 is illustrated for performing surgery on a patient. The version shown in FIG. 1 includes a surgical navigation system 20. The surgical navigation system 20 is shown in a surgical setting such as an operating room of a medical facility. The surgical navigation system 20 is set up to track movement of various objects in the operating room. Such objects include, for example, a surgical instrument 22, a femur F of the patient, a tibia T of the patient, and/or a robotic manipulator 56. The surgical navigation system 20 tracks these objects for purposes of displaying their relative positions and orientations to the surgeon and, in some cases, for purposes of controlling or constraining movement of the surgical instrument 22 relative to virtual cutting boundaries associated with the femur F and tibia T.

The surgical navigation system 20 includes a computer cart assembly 24 that houses a navigation computer 26. A navigation interface is in operative communication with the navigation computer 26. The navigation interface includes a first display 28 adapted to be situated outside of the sterile field and a second display 29 adapted to be situated inside the sterile field. The displays 28, 29 are adjustably mounted to the computer cart assembly 24. First and second input devices (not shown) such as a keyboard and mouse can be used to input information into the navigation computer 26 or otherwise select/control certain aspects of the navigation computer 26. Other input devices are contemplated including a touch screen 30, gesture control, or voice-activation.

A localizer 34 communicates with the navigation computer 26. In the embodiment shown, the localizer 34 is an optical localizer and includes a camera unit 36 (one example of a sensing device). The camera unit 36 has an outer casing 38 that houses one or more optical position sensors 40. The optical sensors 40 may be rigidly mounted to a common support structure. The outer casing 38 may provide the common support structure for the optical sensors 40. Alternatively, a rigid support structure common to the optical sensors 40 may be encased by, but distinct from, the outer casing 38. As illustrated in FIG. 1, the optical sensors 40 are disposed at opposite ends of the elongated camera unit 36, such that the optical sensors are arranged stereoscopically and separated by a separation distance. Representative separation distances may be greater than about 6 inches, greater than about 8 inches, greater than about 12 inches, or greater than about 24 inches. Larger separation distances may improve the three-dimensional depth perception of the system at the cost of larger component size. The larger the size of the camera unit 36 may increase the difficulty of arranging the camera unit 36 to maintain an obstruction-free view of the target space. In some embodiments at least two optical sensors 40 are employed. The optical sensors 40 are capable of variable attenuation of radiant energy, for example, light, into signals as small bursts of electrical current that convey information.

The camera unit 36 may also include a video camera 41 or other additional sensing device. The video camera 41 may be one or more full-color optical sensors, including one or more charge-coupled devices (CCD), complimentary metal-oxide semiconductor (CMOS) active-pixel sensors, and the like. The video camera 41 may provide real-time or low latency video monitoring of the surgical operation. The video camera 41 may include similar or different optical sensing technology as those employed in the optical sensors 40. For example, the optical sensors 40 may be adapted to sense light in the infrared or near-infrared spectrum, while the video camera 41 may be adapted to sense light in the visible spectrum. In an alternative, the optical sensors 40 and the video camera 41 may include similar CMOS sensors adapted to sense light in the visible spectrum.

In some embodiments at least two optical sensors 40 are employed, alternatively, three or four optical sensors 40 may be employed. The optical sensors 40 may be separate CCDs. In some embodiments, two-dimensional CCDs are employed and in other embodiments, one-dimensional CCDs are employed. In some cases, the two, two-dimensional optical sensors 40 are arranged for stereoscopic operation. In some embodiments, a single optical sensor 40 may be provided in combination with depth sensors, laser range finders, and the like. In some other embodiments, a single optical sensor 40 may be employed if a sufficient number of fiducials are within the sensor view, for example, at least four fiducials, and the geometry of the fiducial distribution is known. It should be appreciated that in other embodiments, separate camera units, each with a separate CCD, or two or more CCDs, could also be arranged around the operating room. The optical sensors 40 may include CCDs capable of detecting infrared (IR) radiant energy. In alternative embodiments, the optical sensors 40 may employ other technology, including, but not limited to, complimentary metal-oxide semiconductor (CMOS) active-pixel sensors, and the like.

The camera unit 36 may be mounted on an adjustable arm or other articulated support structure of the cart assembly 24 to selectively position the localizer 34 with a, preferably unobstructed, field of view of the target space including the surgical setting within which will be the patient anatomy and trackers, as discussed below. In some embodiments, the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 may be in further communication with the video camera 41. Alternatively, a separate controller from the camera controller 42 may be provided as a machine vision controller to communicate video information from the video camera 41 to the navigation computer 26. In one embodiment, the machine vision controller in communication with the video camera 41 and the navigation controller are integrally provided on a single printed-circuit board assembly, such as is illustrated in FIG. 1. The integrated controller handling navigation and machine vision will be referred to as the camera controller 42.

The camera controller 42 communicates with the navigation computer 26 through either a wired or a wireless connection (not shown). One such connection may be an IEEE 1394 interface, which is a serial bus interface standard for high-speed communications and isochronous real-time data transfer. The connection could also use a company specific protocol. In other embodiments, the optical sensors 40 may communicate directly with the navigation computer 26, such that the navigation computer incorporates the functionality of, and thus operates as, the camera controller 42. Processing of the signals from the optical sensors 40 and the video camera 41 may occur at the camera controller 42. Alternatively, the camera controller 42 may communicate the signals to the navigation computer 26 for processing for both navigation and machine vision.

The navigation computer 26 can be a personal computer or laptop computer. Navigation computer 26 has the display 28, central processing unit (CPU) and/or other processors, memory (not shown), and storage (not shown). The navigation computer 26 is loaded with software as described below. The software converts the signals received from the camera unit 36 into data representative of the position and orientation of the objects being tracked. Additionally, the software converts the signals received from the camera unit 36 into data that can identify the objects, such as through object recognition from the video camera 41. Position and orientation signals and/or data are transmitted to the navigation computer 26 for purposes of tracking objects. In an alternative, all of the computer processing components and functionality may be integrated into a single processing units, or may be distributed between or among multiple processing units. Moreover, although described as taking place at a particular computer or controller in the present disclosure, it will be appreciated by one of skill in the art that any processing tasks may take place or be performed by other computers or controllers. The computer cart assembly 24, display 28, and camera unit 36 may be like those described in U.S. Pat. No. 7,725,162 to Malackowski, et al. issued on May 25, 2010, entitled "Surgery System," hereby incorporated by reference.

The surgical system 10 illustrated in FIG. 1 includes a plurality of tracking devices 44, 46, 48, also referred to herein as trackers. In the illustrated embodiment, one tracker 44 is coupled to the femur F of the patient and another tracker 46 is coupled to the tibia T of the patient. Trackers 44, 46 may be attached to the femur F and tibia T in the manner shown in U.S. Pat. No. 7,725,162 to Malackowski, et al. issued on May 25, 2010, entitled "Surgery System," hereby incorporated by reference. Trackers 44, 46 could also be mounted like those shown in U.S. Patent Application Publication No. 2014/0200621, published on Jul. 17, 2014, entitled, "Navigation Systems and Methods for Indicating and Reducing Line-of-Sight Errors," hereby incorporated by reference herein. In additional embodiments, a tracker (not shown) is attached to the patella to track a position and orientation of the patella. In other embodiments, the trackers 44, 46 could be mounted to other tissue types or parts of the anatomy according to the needs of a particular operation.

An instrument tracker 48 is coupled to the surgical instrument 22. The instrument tracker 48 may be integrated into the surgical instrument 22 during manufacture or may be separately mounted to the surgical instrument 22 in preparation for the surgical procedures. The working end of the surgical instrument 22, which is being tracked by virtue of the instrument tracker 48, may be an energy applicator EA such as a rotating bur, saw blade, electrical ablation device, or the like. The energy applicator EA may be a separate component such as a bur, saw blade, ablator, or the like that is releasably connected to a handpiece of the surgical tool 22 or may be integrally formed with the handpiece.

The trackers 44, 46, 48 may be active trackers or passive trackers. Active trackers require a power source and have an array of fiducials (also referred to as tracking elements or markers) that actively generate and emit radiation in a wavelength detectable by the optical sensors 40. The fiducials of an active tracker may be a light emitting diode (LED), including, for example, an infrared LED. The array of active fiducials may be "always on" or may be operative to selectively fire, that is emit radiation, according to and in response to commands from the surgical navigation system 20. In such selective-fire active trackers, the tracker may communicate by way of a wired or a wireless connection with the navigation computer 26 of surgical navigation system 20. In alternative embodiments, the tracker may include passive trackers. That is, the array of passive trackers focus or reflect ambient radiation or radiation that has been emitted into the target space, for example by one or more infrared LEDs provided on the camera unit 36 or elsewhere associated with the surgical system 10. The active tracker may be battery powered with an internal battery or may have leads to receive power through the navigation computer 26, which, like the camera unit 36, may receive external power. The passive tracker array typically does not require a power source.

In the embodiment shown, the surgical instrument 22 is attached to a surgical manipulator 56. Such an arrangement is shown in U.S. Pat. No. 9,119,655, issued Sep. 1, 2015, entitled, "Surgical Manipulator Capable of Controlling a Surgical Instrument in Multiple Modes", the disclosure of which is hereby incorporated by reference.

In other embodiments, the surgical instrument 22 may be manually positioned by only the hand of the user, without the aid of any cutting guide, jig, or other constraining mechanism such as a manipulator or robot. Such a surgical instrument is described in U.S. Pat. No. 9,707,043, issued Jul. 18, 2017, the disclosure of which is hereby incorporated by reference.

The optical sensors 40 of the localizer 34 receive signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs 50. In some embodiments, the light signals from the LEDs 50 are fired at different rates for each tracker 44, 46, and 48. In other embodiments, the LEDs 50 are always-on, active tracking elements or markers.

Initially, the objects to be located are viewed by the optical sensors 40 and video camera 41 and identified. The objects may be identified by selecting the objects to be tracked using an input device connected to the navigation computer 26. The navigation computer 26 may store detailed information regarding numerous objects in memory or data storage on the navigation computer 26 and the user may be able to manually select the objects to be tracked from a database of objects.

Additionally, or alternatively, the navigation computer 26 may identify the objects to be tracked based on a pre-operative surgical plan. In this case, the navigation computer 26 may have a preset list of workflow objects that may be used in the pre-scripted surgical workflow. The navigation computer 26 may actively search for and locate the workflow objects using software in the image data provided by the optical sensors 40 or video camera 41. For instance, groups of pixels associated with different sizes and shapes of the various objects may be stored in the navigation computer 26. By selecting/identifying the objects to be located/tracked, the software identifies the corresponding group of pixels and the software then operates to detect like groups of pixels using conventional pattern recognition technology.

Additionally, or alternatively, the objects to be located/tracked can be identified using an interface in which one of the participants outlines or selects the objects to be tracked on one or more of the displays 28, 29. For instance, images taken by the optical sensors 40, or video camera 41, of the surgical site may be displayed on one or more of the displays 28, 29 (and/or other displays). The participant then, using a mouse, digital pen, or the like, traces objects to be located/tracked on the display 28 and/or 29. The software stores the pixels associated with the object that was traced into its memory. The participant (or other user) may identify each object by a unique identifier such as naming the object using the software so that the saved group of pixels may be associated with the unique identifier. Multiple objects could be stored in this manner. The navigation computer 26 utilizes conventional pattern recognition and associated software to later detect these objects. The navigation system 20 is able to detect movement of these objects by continuously taking images, reviewing the images, and detecting movement of the groups of pixels associated with the objects.

The objects to be tracked may be initially located and registered using a navigation pointer P. For example, the navigation pointer P may have an integrated tracker PT. The navigation computer 26 may store initial data corresponding to a location of the tip of the pointer P relative to the tracker PT such that the navigation system 20 is able to locate and track the tip of the pointer P in the localizer coordinate system LCLZ. Accordingly, prior to the start of the surgical procedure, once all the objects are located in their desired locations, one of the participants may touch all of the objects with the pointer P, while identifying the objects in the navigation system 20 using one of the input devices described above. For example, when the participant touches the surgical instrument 22 with the tip of the pointer P, the participant may simultaneously trigger collection of that point in the localizer coordinate system LCLZ (via another input device, such as a foot pedal). When the point is collected, the participant can also enter into the navigation software the identity of the object (via typing, pull-down selection from a list of objects, etc.).

The machine vision system is incorporated into the navigation system 20. More specifically, the machine vision system may include a machine vision controller that is coupled to the navigation computer 26, or may be integrated with the camera controller 42. The machine vision system includes one or more machine vision cameras coupled to the machine vision controller, such as the video camera 41 coupled to the camera controller 42. While one video camera 41 is illustrated in FIG. 1, it should be recognized that any suitable number of video cameras 41 or other optical sensors may be included within the machine vision system. The video cameras 41 may be CCDs or CMOS sensor-based cameras or other forms of machine vision camera. In some cases, the video cameras are arranged for stereoscopic operation, or single cameras combined with depth sensors, laser range finders, and the like, may be used.

Machine vision can identify and locate various objects in the operating room. The video camera 41 (and in some cases, depth sensors) can be arranged to determine 3-D positions and/or orientations of the objects in a machine vision coordinate system. In the example illustrated in FIG. 1, the video camera 41 providing machine vision is rigidly supported with the optical sensors 40 in a known and predefined relationship according to the manufacturing of the camera unit 34. The video camera 41 and optical sensors 40 are arranged so that their field-of-view encompasses the objects in the operating room. By way of non-limiting example, the objects may include a robotic manipulator 56, one or more surgical instruments 22, portions of the patient's anatomy (e.g., tibia T and femur F), and/or any other suitable object. In providing an integrated camera unit 34, the need to operate in and transform between a machine vision coordinate system and a navigation coordinate system can be alleviated or eliminated. More specifically, the machine vision coordinate system and the navigation coordinate system may be the same coordinate system. In the embodiment described in FIG. 1, the machine vision coordinate system and the navigation coordinate system are the same and collectively identified as the localizer coordinate system LCLZ, described in more detail below.

Initially, the objects to be located are viewed by the video camera 41 and optical sensors 40 and identified. The objects may be identified by selecting the objects to be tracked using an input device connected to the navigation computer 26. The navigation computer 26 may store detailed information regarding numerous objects in memory on navigation computer 26 or the camera controller 42 and the user may be able to manually select the objects to be tracked from a database of objects.

Additionally, or alternatively, the machine vision controller 14 may identify the objects to be tracked based on a pre-operative surgical plan. In this case, the navigation computer 26 may have a preset list of workflow objects that may be used in the pre-scripted surgical workflow. The navigation computer 26 may actively search for and locate the workflow objects using machine vision software. For instance, groups of pixels associated with different sizes and shapes of the various objects may be stored in the navigation computer 26. By selecting/identifying the objects to be located/tracked, the machine vision software identifies the corresponding group of pixels and the machine vision software then operates to detect like groups of pixels using conventional pattern recognition technology.

Additionally, or alternatively, the objects to be located/tracked can be identified using an interface in which one of the participants outlines or selects the objects to be tracked on one or more of the displays 28, 29. For instance, images taken by the video camera 41 or optical sensors 40 from overhead the surgical site may be displayed on one or more of the displays 28, 29 (and/or other displays). The participant then, using a mouse, digital pen, or the like, traces objects to be located/tracked on the display 28 and/or 29. The machine vision software stores the pixels associated with the object that was traced into its memory. The participant (or other user) may identify each object by a unique identifier such as naming the object using the machine vision software so that the saved group of pixels may be associated with the unique identifier. Multiple objects could be stored in this manner. The navigation computer 26 utilizes conventional pattern recognition and associated software to later detect these objects in the image data provided by the video camera 41 or the optical sensors 40.

The navigation system 20 is able to detect movement of these objects by continuously taking images, reviewing the images, and detecting movement of the groups of pixels associated with the objects. In some cases, location information from the camera controller 42 for the objects can be transmitted to the navigation computer 26. Likewise, location information from the navigation computer 26 can be transmitted from the navigation computer 26 to the camera controller 42.

After the navigation system 20 identifies and locates any desired objects within the operating room, the navigation computer 26 may transmit the location and identity of the objects to the camera controller 42. The navigation computer 26 and/or the camera controller 42 uses the location and identity of the objects to selectively adjust the localizer 34, including the data output from one or more of the optical sensors 40 or video camera 41 to focus on the portion of the operating room that includes the objects. Thus, the navigation system 20 may disregard other areas of the operating room as described more fully herein, thus improving a processing and tracking efficiency of the navigation system 20.

Figure 2:
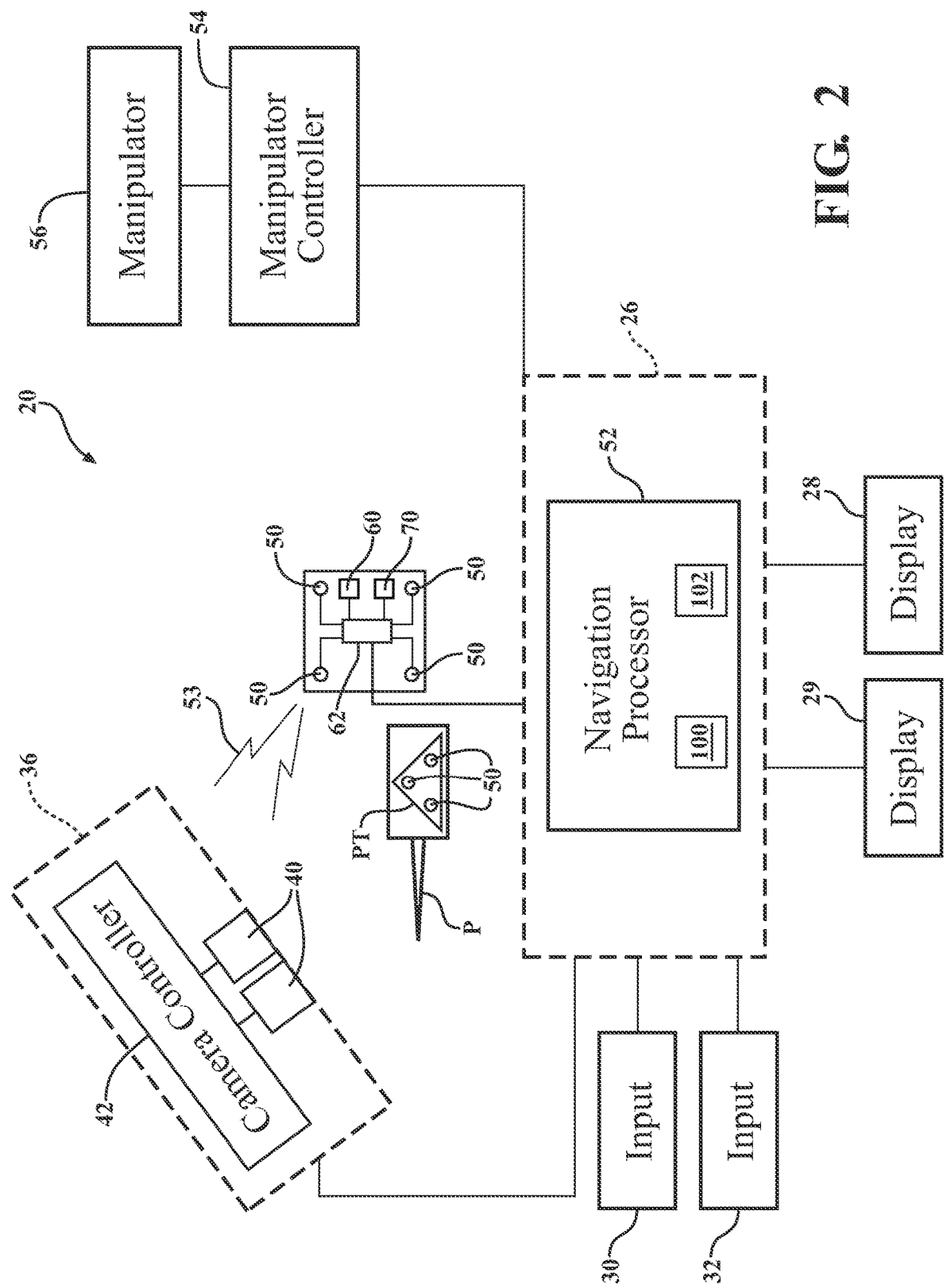
FIG. 2 is a schematic view of the navigation system.

Referring to FIG. 2, a schematic view of a control system for controlling the surgical navigation system 20 and robotic surgical device 56 is shown. In this schematic, each of the LEDs 50 are illustrated connected to a tracker controller 62 located in a housing (not shown) of the associated tracker 44, 46, 48 that transmits/receives data to/from the navigation computer 26 and/or camera controller 42. In one embodiment, the tracker controllers 62 transmit data through wired connections with the navigation computer 26. In other embodiments, a wireless connection may be used. In these embodiments, the navigation computer 26 has a transceiver (not shown) to receive the data from the tracker controller 62. In other embodiments, the trackers 44, 46, 48 may have passive markers (not shown), such as reflectors that reflect light, for example, light emitted by an LED provided on camera unit 36. For example, the camera unit 36 may include complementary emitters in a wavelength to which the optical sensors 40 are sensitive. The reflected light is then received by the optical sensors 40. In some embodiments, the trackers 44, 46, 48 may also include a gyroscope sensor 60 and accelerometer 70, such as the trackers shown in U.S. Pat. No. 9,008,757 to Wu, et al., issued on Apr. 14, 2015, entitled, "Navigation System Including Optical and Non-Optical Sensors," the entire disclosure of which is hereby incorporated by reference. These additional sensors 60, 70, may provide information to the navigation computer 26 for use by the navigation computer 26 to determine or track the trackers' 44, 46, 48 position or orientation.

The navigation computer 26 includes a navigation processor 52. It should be understood that the navigation processor 52 could include one or more processors to control operation of the navigation computer 26, may perform one or more navigation functions, and may perform one or more machine vision functions. The processors can be any type of microprocessor or multi-processor system. The term "processor" is not intended to limit the scope of the invention to a single processor or to any particular function.

As illustrated in FIG. 2, the camera unit 36 receives optical signals 53 from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some embodiments), navigation processor 52 generates data indicating the relative positions and orientations of the trackers 44, 46, 48 relative to the localizer 34.

Prior to the start of the surgical procedure, additional data are loaded into the navigation processor 52. Based on the position and orientation of the trackers 44, 46, 48 and the previously loaded data, navigation processor 52 determines the position of the working end of the surgical instrument 22 (e.g., the centroid of a surgical bur) and the orientation of the surgical instrument 22 relative to the tissue against which the working end is to be applied. In some embodiments, navigation processor 52 forwards the data to a manipulator controller 54. The manipulator controller 54 can then use the data to control a robotic manipulator 56 as described in U.S. Pat. No. 9,119,655 to Bowling, et al., incorporated above.

The navigation processor 52 also generates image signals that indicate the relative position of the surgical instrument working end to the tissue. These image signals are applied to the displays 28, 29. Displays 28, 29, based on these signals, generate images that allow the surgeon and staff to view the relative position of the surgical instrument working end to the surgical site. The displays, 28, 29, as discussed above, may include a touch screen 30 or other input/output device that allows entry of commands.

In the embodiment shown in FIG. 1, the surgical tool 22 forms part of an end effector of the manipulator 56. The manipulator 56 has a base 57, a plurality of links 58 extending from the base 57, and a plurality of active joints (not numbered) for moving the surgical tool 22 with respect to the base 57. The links 58 may form a serial arm structure as shown in FIG. 1, a parallel arm structure (not shown), or other suitable structure. The manipulator 56 has the ability to operate in a manual mode in which a user grasps the end effector of the manipulator 56 in order to cause movement of the surgical tool 22 (e.g., directly, through force/torque sensor measurements that cause active driving of the manipulator 56, or otherwise) or a semi-autonomous mode in which the surgical tool 22 is moved by the manipulator 56 along a predefined tool path (e.g., the active joints of the manipulator 56 are operated to move the surgical tool 22 without requiring force/torque on the end effector from the user). An example of operation in a semi-autonomous mode is described in U.S. Pat. No. 9,119,655 to Bowling, et al., incorporated above. A separate tracker (not shown) may be attached to the base 57 of the manipulator 56 to track movement of the base 57.

The manipulator controller 54 may have a central processing unit (CPU) and/or other manipulator processors, memory (not shown), and storage (not shown). The manipulator controller 54, also referred to as a manipulator computer, is loaded with software. The manipulator processors could include one or more processors to control operation of the manipulator 56. The manipulator 56 may be in the form of a conventional robotic system or other conventional machining apparatus, and thus the components thereof shall not be described in detail. In one embodiment, when the manipulator 56 is operated in the semi-autonomous mode, the manipulator 56 is capable of moving the surgical tool 22 free of operator assistance. Free of operator assistance may mean that an operator/user does not physically contact the surgical tool 22 to move the surgical tool 22. Instead, the operator may use some form of remote control to control starting and stopping of movement. For example, the operator may hold down a button of the remote control to start movement of the surgical tool 22 and release the button to stop movement of the surgical tool 22.

In the manual mode, in one embodiment, the operator physically contacts the end effector to cause movement of the surgical tool 22. The manipulator controller 54 can use the position and orientation data of the surgical tool 22 and the patient's anatomy to control the manipulator 56 as described in U.S. Pat. No. 9,119,655 to Bowling, et al., incorporated above.

The manipulator controller 54 determines the desired location to which the surgical tool 22 should be moved. Based on this determination, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers (not shown) (e.g., one for controlling each motor) that control the active joints of the manipulator 56 to move the plurality of links 58 and thereby move the surgical tool 22 from the current location to the desired location.

Figure 3:
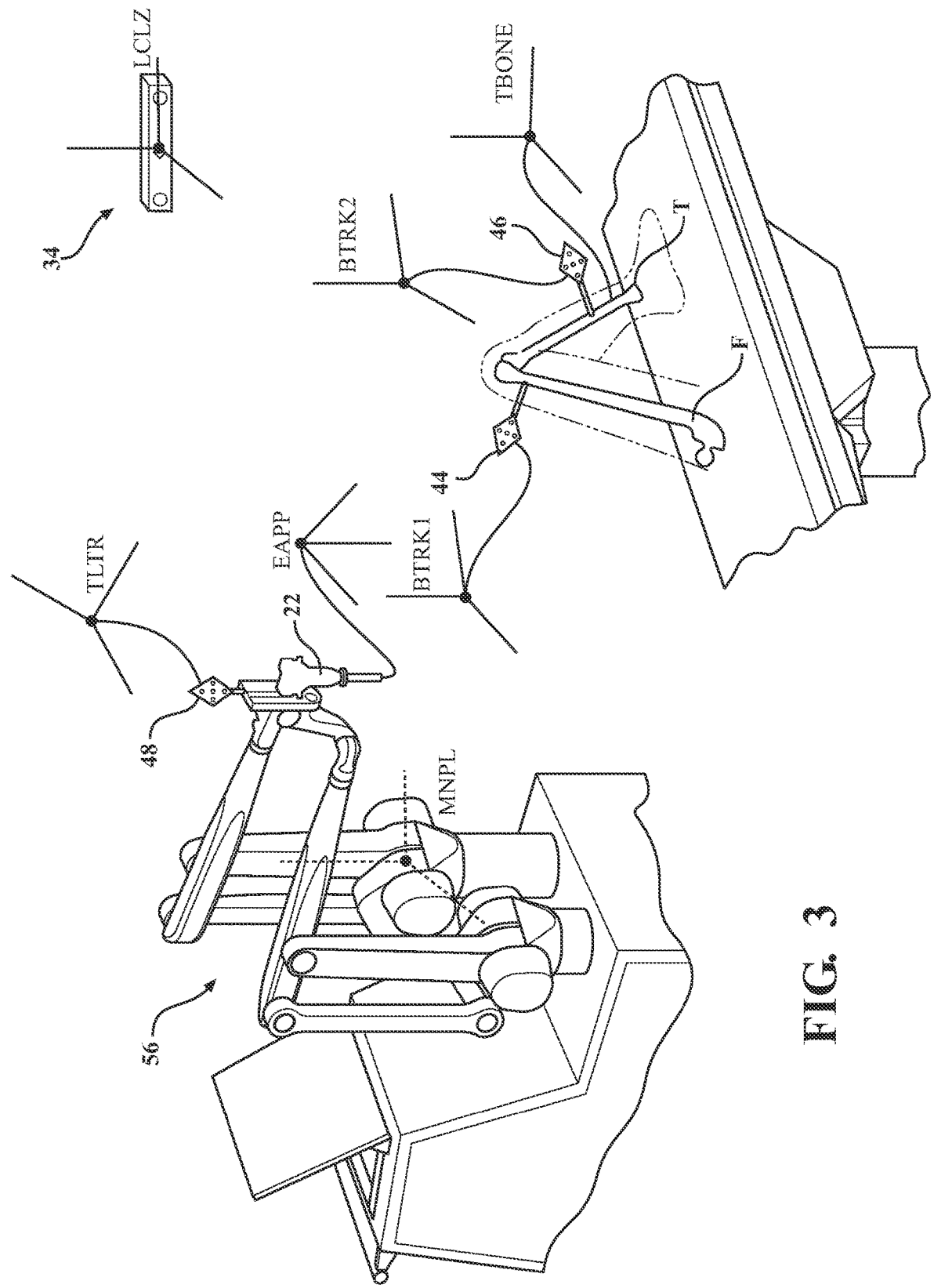
FIG. 3 is schematic view of the coordinate systems used in the navigation system.

Referring to FIG. 3, tracking of objects is generally conducted with reference to a localizer coordinate system LCLZ. The localizer coordinate system has an origin and an orientation (a set of x-, y-, and z-axes). During the procedure, one goal is to keep the localizer coordinate system LCLZ in a known position. An accelerometer (not shown) mounted to the camera unit 36 may be used to track sudden or unexpected movement of the localizer coordinate system LCLZ, as may occur when the camera unit 36 is inadvertently bumped by surgical personnel.

Each tracker 44, 46, 48 and object being tracked also has its own coordinate system separate from localizer coordinate system LCLZ. Components of the navigation system 20 that have their own coordinate systems are the bone trackers 44 and 46, and the instrument tracker 48. These coordinate systems are represented as, respectively, bone tracker coordinate systems BTRK1 and BTRK2, and instrument tracker coordinate system TLTR.

Navigation system 20, through the localizer 34, monitors the positions of the femur F and tibia T of the patient by monitoring the position of bone trackers 44, 46 coupled to bone. The femur coordinate system is FBONE and the tibia coordinate system is TBONE, which are the coordinate systems of the bones to which the bone trackers 44, 46 are coupled.

Prior to the start of the procedure, pre-operative images of the femur F and tibia T are generated (or of other tissues in other embodiments). These images may be based on MRI scans, radiological scans or computed tomography (CT) scans of the patient's anatomy. These images are mapped to the femur coordinate system FBONE and tibia coordinate system TBONE using well-known methods in the art. These images are fixed in the femur coordinate system FBONE and tibia coordinate system TBONE. As an alternative to taking pre-operative images, plans for treatment can be developed in the operating room (OR) from kinematic studies, bone tracing, and other methods.

During an initial phase of the procedure, the bone trackers 44, 46 are coupled to the bones of the patient. The pose (position and orientation) of coordinate systems FBONE and TBONE must be mapped to coordinate systems BTRK1 and BTRK2, respectively. Given the fixed relationship between the bones and their bone trackers 44, 46, positions and orientations of the femur F and tibia T in the femur coordinate system FBONE and tibia coordinate system TBONE must be transformed to the bone tracker coordinate systems BTRK1 and BTRK2 so the camera unit 36 is able to track the femur F and tibia T by tracking the bone trackers 44, 46. This pose-describing data are stored in memory integral with both manipulator controller 54 and navigation processor 52.

The working end of the surgical instrument 22 (also referred to as energy applicator distal end) has its own coordinate system EAPP. The origin of the coordinate system EAPP may represent a centroid of a surgical cutting bur, for example. The pose of coordinate system EAPP must be fixed to the pose of instrument tracker coordinate system TLTR before the procedure begins. Accordingly, the poses of these coordinate systems EAPP, TLTR relative to each other must be determined in the navigation computer 26. The pose-describing data are stored in memory integral with both manipulator controller 54 and navigation processor 52.

Referring back to FIG. 2, a localization engine 100 is a software module that may be included within the navigation system 20. Components of the localization engine 100 may execute on navigation processor 52. In some embodiments, however, the localization engine 100 may execute on the manipulator controller 54 or camera controller 42.

Localization engine 100 receives as inputs the optically based signals from the camera controller 42 and, in some embodiments, the non-optically based signals from the tracker controller 62. Based on these signals, localization engine 100 determines the pose of the bone tracker coordinate systems BTRK1 and BTRK2 in the localizer coordinate system LCLZ. Based on the same signals received for the instrument tracker 48, the localization engine 100 determines the pose of the instrument tracker coordinate system TLTR in the localizer coordinate system LCLZ.

The localization engine 100 forwards the signals representative of the poses of trackers 44, 46, 48 to a coordinate transformer 102. Coordinate transformer 102 is a navigation system software module that runs on navigation processor 52. Coordinate transformer 102 references the data that defines the relationship between the pre-operative images of the patient and the bone trackers 44, 46. Coordinate transformer 102 also stores the data indicating the pose of the working end of the surgical instrument relative to the instrument tracker 48.

During the procedure, the coordinate transformer 102 receives the data indicating the relative poses of the trackers 44, 46, 48 to the localizer 34. Based on these data and the previously loaded data, the coordinate transformer 102 generates data indicating the relative position and orientation of the coordinate system EAPP, the machine vision coordinate system MV, and the bone coordinate systems, FBONE and TBONE to the localizer coordinate system LCLZ.

As a result, coordinate transformer 102 generates data indicating the position and orientation of the working end of the surgical instrument 22 relative to the tissue (e.g., bone) against which the instrument working end is applied. Image signals representative of these data are forwarded to displays 28, 29 enabling the surgeon and staff to view this information. In certain embodiments, other signals representative of these data can be forwarded to the manipulator controller 54 to guide the manipulator 56 and corresponding movement of the surgical instrument 22.

In a similar manner, other trackers may be coupled to any other suitable object to be tracked within the operating room, and each object and associated tracker may be registered to the localizer coordinate system LCLZ as described above.

Figure 4:
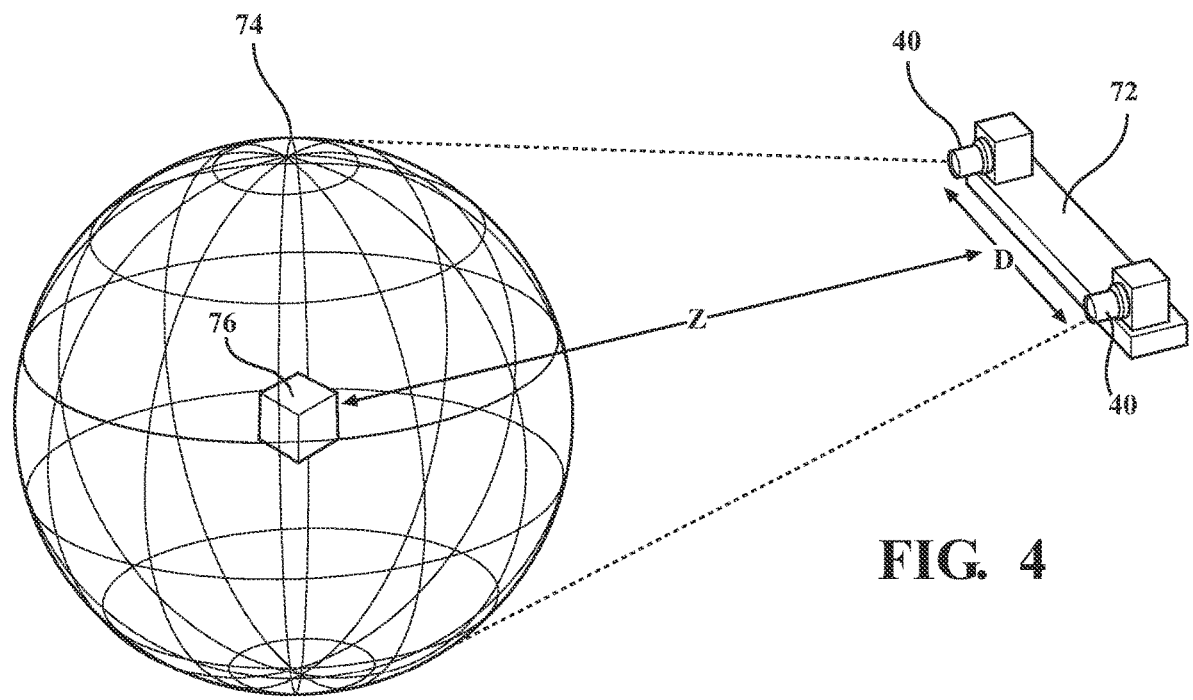
FIG. 4 is a schematic view showing the relationship between optical sensors and a working space.

Referring to FIG. 4, a representation of the relationship of the optical sensors 40 to the target space is represented. In the illustrated embodiment, two, two-dimensional optical sensors 40 are arranged for stereoscopic operation, mounted to a common support structure 72 and separated by a separation distance D. The common support structure 72 may be enclosed within housing 38 (shown in FIG. 1). The optical sensors 40 are arranged with a view of the working space 74. Within the working space 74, an element is provided as a region of interest 76. In a surgical operation, the region of interest 76 may be a particular area of a patient's anatomy upon which the procedure is focused. The region of interest 76 may encompass the entirety of the optical sensors' 40 field of view, or alternatively, may be a portion of the full field of view 74.

Figure 5:
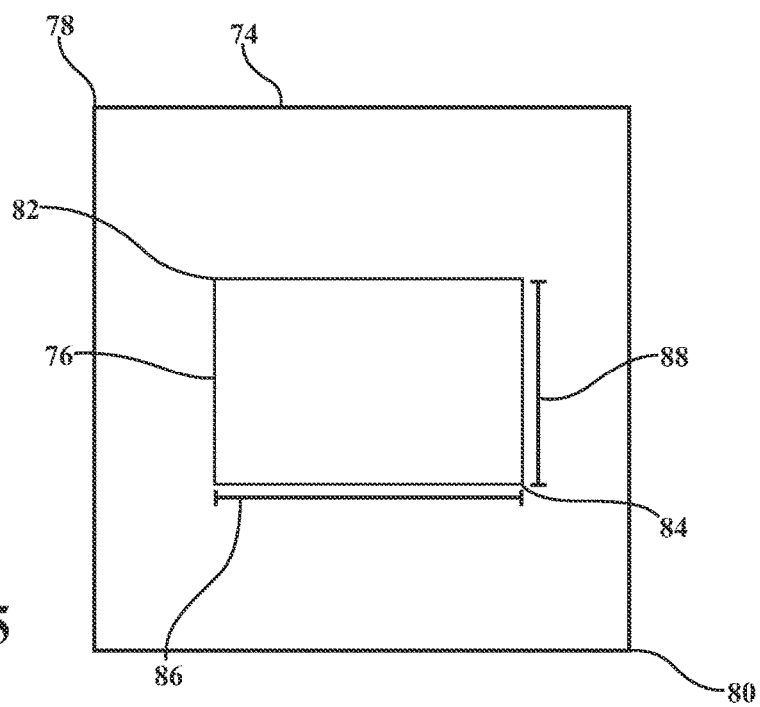
FIG. 5 is a schematic view of an arrangement of sensing elements.

Referring to FIG. 5, a representation of the optical sensor's 40 field of view of the working space 74 is shown projected as it would be incident on the sensor elements of the optical sensor 40, with a particular region of interest 76 also illustrated. In some embodiments, the optical sensors 40 include a printed circuit board assembly (PCBA) having an array of charge-coupled sensor elements. Each sensor element may be uniquely identifiable according to an addressable location on the sensor. For example, the sensor elements may be identifiable in an x-coordinate and y-coordinate according to the number of rows and number of columns of elements on the sensor. Specifically, a first sensor element 78 in an arbitrary top-left corner may be identified with the coordinate (1, 1), while the last sensor element 80 in the opposite, bottom-right corner may be identified with the coordinate (1000, 1000), for a sensor having 1,000 rows and 1,000 columns of individual sensor elements. In this example, the sensor would therefore be characterized as a 1 megapixel (MP) optical sensor, having one million active sensor elements. Each sensor element corresponds to one pixel of information contributing to the output of the sensor. The sensor array may typically form a rectangular or square array.

The region of interest 76 is present within a subset of the sensor elements. The region of interest 76 may be located by identifying a beginning pixel 82 and an ending pixel 84 on the sensor on which the region of interest 76 acts. As shown in FIG. 5, the region of interest may be located across the pixels (201, 301) (shown at 82 in FIG. 5) to (800, 700) (shown at 84 in FIG. 5). This region forms an array having a width 86 of 600 pixels wide and having a height 88 of 400 pixels tall. The region of interest therefore occupies 0.24 MP of the 1 MP sensor. In reading out information from the sensor, defined by the range of sensor elements within the region of interest 76, the data processing load is therefore 24% of the data processing load of the full range of active sensor elements in the working space 74. A reduction in the data processing load provides a corresponding increase in the data processing cycle speed. That is, each cycle of processing the image data consumes less time as the amount of data to process is reduced.

Figure 6:
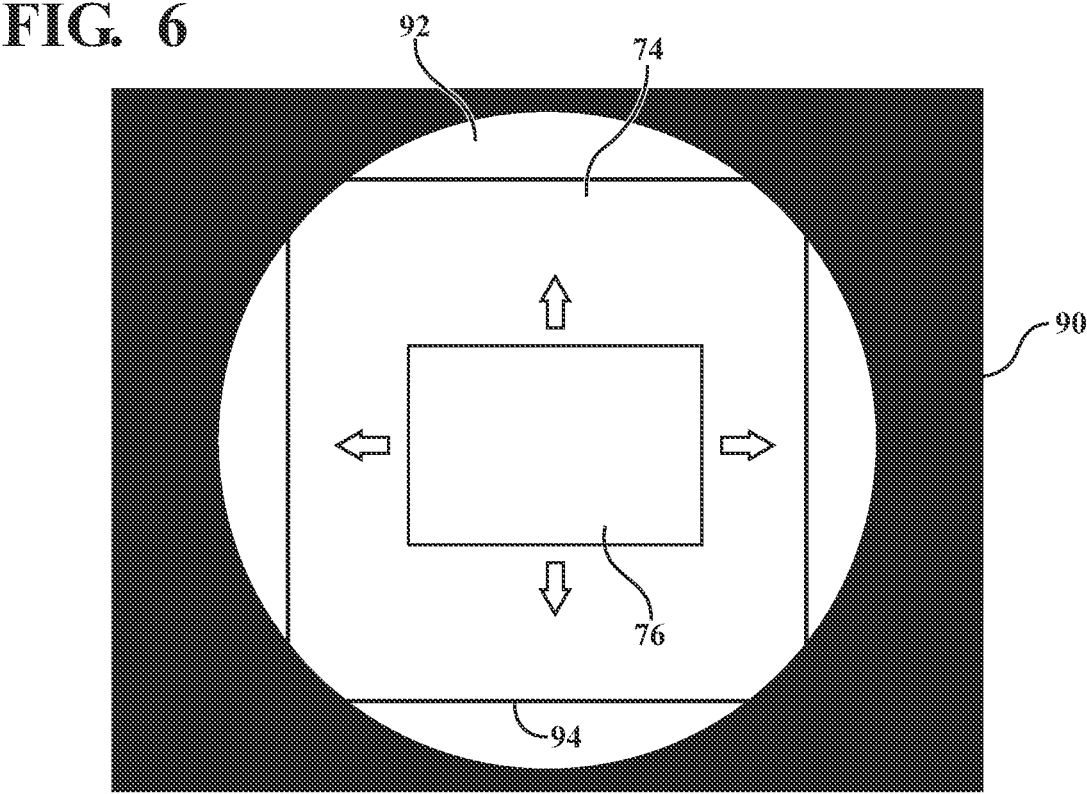
FIG. 6 is a representative view of light incident on an optical sensor.

Supported within the housing 38 and between the sensor PCBA of each optical sensor 40 and the physical volume in which the surgeon operates, an optic element, such as a lens, is provided to focus incident radiant energy onto the sensor elements. In some embodiments, a single lens is provided macroscopically over the PCBA, and in other embodiments, microlenses may be provided over each individual sensor element. The lens may be static, or may be adjustable to more precisely focus the energy onto the sensor elements. This relationship is shown in FIG. 6. The total array of sensor elements provided on the PCBA is represented by the rectangular area 90. In the example shown, a single lens focuses energy onto a substantially circular area 92 of sensor elements. The sensor elements disposed outside this circular area may be blocked by the housing 38, and thus considered inactive. The camera controller 42 may be configured to exclude any inactive pixels when reading information from the optical sensor. Moreover, the camera controller 42 may also exclude sensor elements within the scope of the lens focus to create a rectangular or square array 94 of indexed elements. The indexed array 94 of sensor elements is within the focused area of the lens and forms the field of view of the working space 74 for the optical sensor 40. The region of interest 76 occupies all or a portion of the indexed array 94 of sensor elements. Although illustrated with the region of interest 76 centrally disposed within the field of view of the working space 74, it should be appreciated that the region of interest 76 may comprise alternative portions within the working space 74. Similarly, the region of interest 76 may include larger portions or smaller portions of the working space 74. This improvement allows a larger sensor, that is—one having more sensing elements, and thus a lower frame rate, to be operated at a higher frame rate by using only parts of the sensor within a limited, defined portion of the array of sensing elements.

Figure 7:
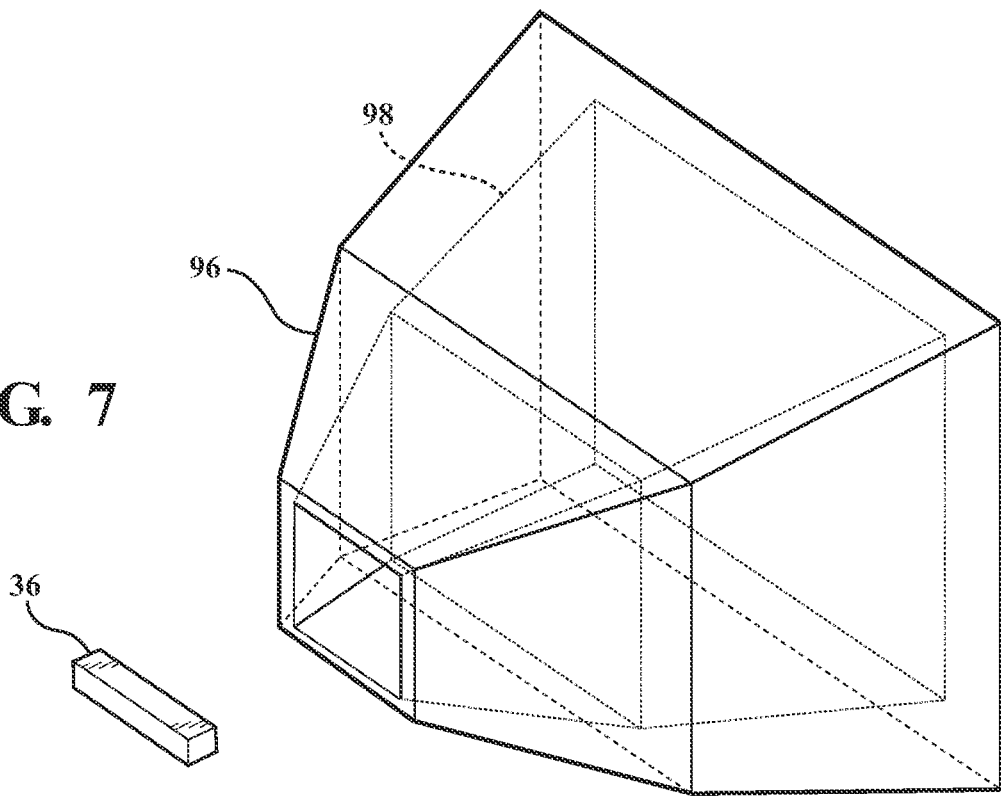
FIG. 7 is a schematic representation of observed volume by a camera unit.

FIG. 7 illustrates the above-described relationship in a three-dimensional perspective representation. Camera unit 36 is schematically represented relative to the field of view of the working space 74. The total volume 96 of the optical sensor encompasses a reduced volume 98 of the region of interest 76. Similar to the depictions in FIGS. 5 and 6, the reduced volume 98 is centrally disposed within the total volume 96. The initial positioning of the camera unit 36 will impact the relative position of the surgical site within the field of view of the camera. It may therefore be preferable that a reduced volume 98 be positioned in one or another corner of the total volume 96. Alternatively, the reduced volume 98 may take up more or less of the total volume 96 depending on the size and location of the surgical site and the distance of the surgical site from the camera unit 36. Where the reduced volume 98 occupies a larger proportion of the total volume 96, a larger portion of the working space 74 is occupied by the region of interest 76 on the optical sensor's 40 sensing elements. Similarly, where the reduced volume 98 occupies a particular corner or region of the total volume 96, a corresponding corner or region of the working space 74 is occupied by the region of interest 76 on the optical sensor's 40 sensing elements.

The total volume projection of the working space within the scope of the optical sensor 40 is related to the hardware configuration of the camera unit 36. For example, a static lens arrangement may affect the focus for determining the closest and farthest observable objects. For example, the observable volume may begin within about 0.5 meters from the camera unit 36 and may extend to up to 3 meters from the camera unit 36. In an alternative example, the observable volume may be at a distance of about 0.7 meters to about 2.5 meters from the camera unit 36. The camera unit 36 may be configured for an optimal focal distance of the region of interest to be from 1 meter to 1.5 meters from the camera unit 36. In an alternative example, the camera unit 36 may be configured to have an optimal focal distance of 1.3 meters from the camera unit.

During navigation in a surgical operation, the navigation computer 26 tracks the location and movement of trackers affixed to objects used during the surgical operation. The navigation computer 26 may use two-dimensional image information received from the optical sensors 40. Optical sensors 40 generate the two-dimensional images from the radiant energy received at the PCBA of the optical sensor. The intensity of radiant energy at each active pixel is quantified to generate the two-dimensional images processed for navigation tracking. Each active pixel evaluated consumes processing time. It is therefore preferable to reduce the number of active pixels, without otherwise adversely affecting image resolution or quality, in order to improve the quality of accurately tracking rapid movement or very fine movement of a tracked object. By defining a region of interest as a subset of the total active elements available within the optical sensors 40, the processing speed may be increased.

In defining only a portion of the available range of the optical sensor 40, it is important to ensure that the region of interest encompasses the objects to be tracked. At an initial phase of a surgical operation, the navigation system 20 may operate to capture one or multiple images of the working space using the full or near-full optical sensor 40 range, or using the video camera 41. At the initial phase, high speed and high accuracy tracking may be deemphasized as a surgeon performs initial setup steps for the surgical operation. Once the surgical operation is underway, the surgeon may selectively toggle to switch the navigation system 20 into a high-speed tracking operational mode. Alternatively, the navigation system 20 may automatically switch between tracking using the full-range of the optical sensor 40 and a more limited region of interest. The navigation system 20 may be configured to switch automatically between operation modes based, for example, on the detection of the object to be tracked, the determined position, orientation, or movement of the tracked object. The navigation system 20 may be configured to switch automatically between operation modes based on an autonomous movement of the surgical manipulator 56.

During operation, the navigation system 20 may be configured to selectively size and position the region of interest 76 within the optical sensors' 40 field of view 74. In this way, the navigation system 20 can limit the volume of data to be processed and improve tracking speed. The navigation system 20 may be configured to determine a pose of each tracker (e.g., tracker 44, 46, 48) attached to each object of interest. Data representative of the identified objects and/or trackers, as well as the pose and movement of each object and/or tracker may be determined and stored by the navigation computer 26; or may be determined by the camera controller 42 and transmitted to the navigation computer 26. The pose and/or movement information of the object and/or tracker may be used to determine the region of interest 76 for navigation tracking.

For example, the navigation processor 52 may first determine the coordinates of the individual sensor elements in each optical sensor 40 that correspond to the present location of each object of interest. Alternatively, the navigation processor 52 may determine the coordinates of the individual sensor elements in the video camera 41 sensing array in the same way as described above with regard to the optical sensor 40. Because the video camera 41 and the optical sensors 40 are housed together within the camera unit 36, the portion of the sensing devices respectively within the video camera 41 and the optical sensors 40 with a view of the object correspond to one another. Therefore, determining a region of interest in the sensing device of the video camera 41 (i.e. the array of sensing elements in which the object appears) informs the region of interest of optical sensors 40. Accordingly, the active size and position of the region of interest 76 within the optical sensors 40 can be updated over time for successive tracking cycles by monitoring, for example, where the object is relatively located within the active pixel arrays of the video camera 41.

The navigation processor may reference a table or other data structure stored within memory of the navigation computer 24 or camera controller 42. The table may identify which sensor elements are activated or otherwise correspond to various coordinate locations within the localizer coordinate system LCLZ. The navigation processor 52 may then identify one or more additional sensor elements within a margin surrounding the sensor elements corresponding to the present position of the object. In one embodiment, the navigation process 52 may determine the number of additional sensor elements within a margin surrounding the present position to achieve a total desired proportion of available sensor elements, for example, 66% of the available sensor elements. It should be appreciated that the navigation processor 52 may define each region of interest 76 to include any suitable proportion of the total available sensor elements to efficiently and accurately track the object, taking into account normal or expected movement of the object. The region of interest may be determined independently for each optical sensor 40.

In some examples, the region of interest 76 may be defined to account for movement within a predetermined movement envelope (e.g., predetermined movement in any one or more of six degrees of freedom from the current pose). The expected movement may be based on prior pose data (e.g., a difference in position over time equating with a velocity and/or an acceleration of the object or tracker). In some embodiments, the expected movement may be based on the type of object being tracked. For example, if the tracker is attached to certain portions of the anatomy (e.g., the pelvis, spine, or skull), the tracker may be expected to move a relatively small amount. If the tracker is attached to other portions of the anatomy (e.g., the tibia in a robotic knee surgery), then the surgeon may move the anatomy in a large range of motion to determine joint stability such that the tracker may be expected to move in a circular range of several centimeters to more than a meter.

Accordingly, the navigation system 20 may need to account for the current pose of each tracker and the expected range of motion of each tracker to set the bounds for the region of interest 76. In one embodiment, each tracker may have a unique identifier that is detectable by the camera unit 36. For example, each tracker may include a quick response (QR) code or other machine-readable code, or each tracker may wirelessly communicate the identifier to the navigation system 12. In an alternative example, the user may enter the identifier (e.g., tibia tracker, femur tracker, pelvis tracker, spine tracker, etc.) during an initial setup phase of the surgical procedure.

Once a current pose of each tracker and the likely range of movement of each tracker is determined, the navigation system 20, the camera controller 42, and/or the navigation processor 52 can then determine a likely region of interest 76 needed for the camera unit 36. For example, the camera controller 42 or the navigation processor 52 may determine a large region of interest 76, including a large margin, for example, about 80% of the available sensor elements, if a tibia tracker 46 is used due to the wider range of movement. However, if the trackers are unlikely to move across a large range, then the region of interest 76 may be set to a smaller size, for example, about 40% of the available sensor elements. As a result, the camera controller 42 or the navigation processor 52 may dynamically update the region of interest 76 based on the type of tracker or object being tracked, the expected movement of the object or tracker, and/or based on the prior pose data (e.g., velocity and/or acceleration) of the object or tracker.

The processing of only a subset of the sensor elements from each optical sensor 40 enables a processing load to be reduced when the navigation processor 52 processes the sensing element signals to track the position and movement of the objects within the operating room. As a result, the localizer may sample the light signals received from the trackers 44, 46, and 48 at a higher frequency than the localizer 34 might otherwise be able to sample if the navigation processor 52 were configured to process all the available sensor elements within the optical sensors 40. For example, processing the sensing elements within the region of interest 76 may occur at a frequency of up to about 1 kHz; whereas processing the sensing elements of the entire working space may occur at a frequency of about 300 Hz. The higher frequency processing provided by the region of interest 76 allows the navigation system to provide higher speed and higher precision tracking of the objects of interest.

While the embodiments described above are described as being performed by one of the camera controller 42 or the navigation processor 52, it should be recognized that the identification and determination of the region of interest 76 and the subset of sensor elements included within and adjacent to the region of interest 76 may be additionally or alternatively performed by another suitable processor or controller in communication with the navigation system 20.

Figure 8:
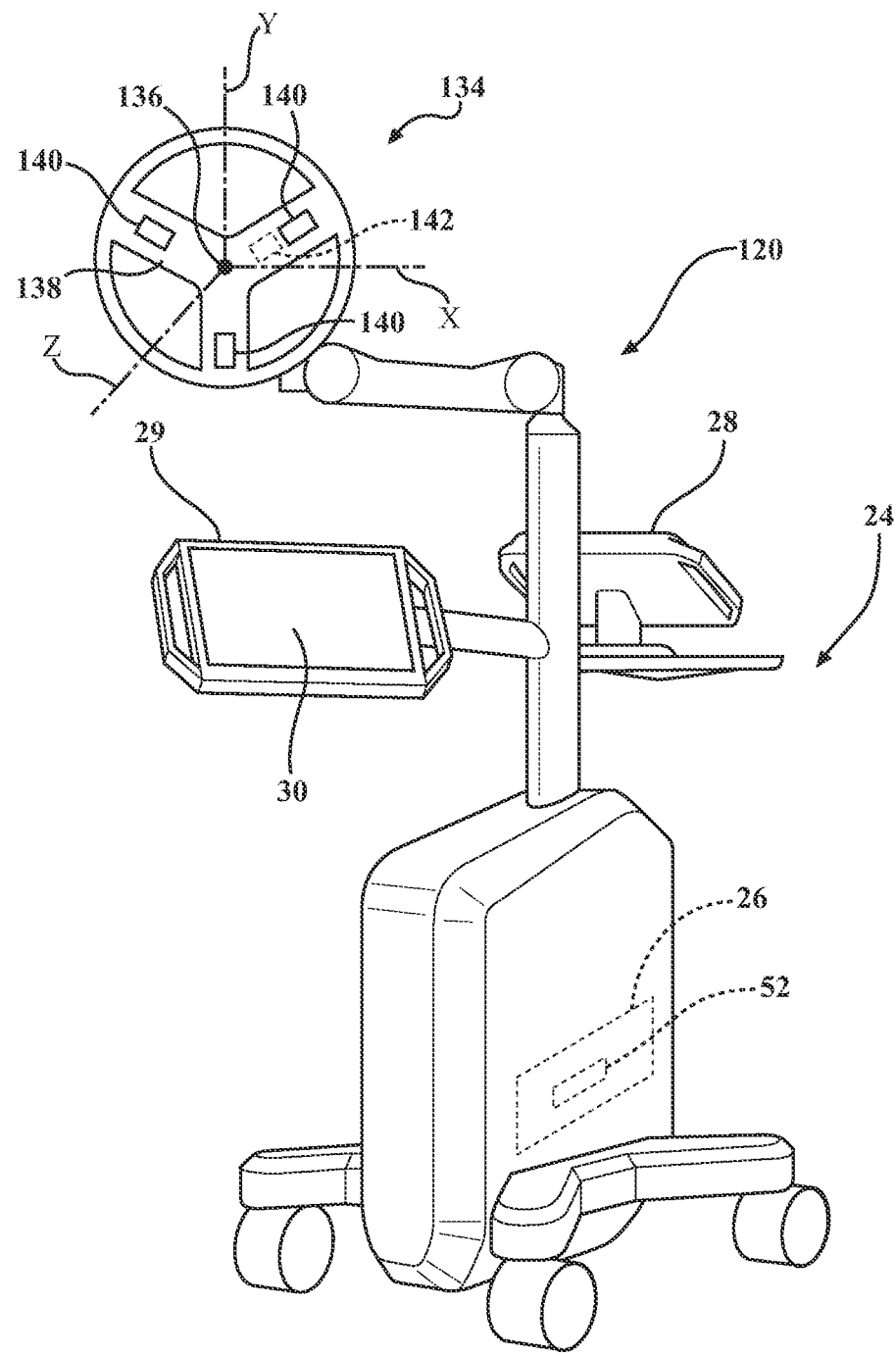
FIG. 8 is a perspective view of a navigation system in an alternative embodiment.

Referring to FIG. 8, an alternative embodiment of a navigation system 120 is illustrated with like components numbered the same. In this embodiment, the navigation system 120 includes camera unit 134 having three one-dimensional optical sensors 140, and a full color video camera 136. A camera controller 142 is in communication with the optical sensors 140 and the video camera 136, providing functionality similar to that described above with regard to camera controller 42. A housing 138 supports and houses the optical sensors 140, the video camera 136, and the camera controller 142.

Figure 9:
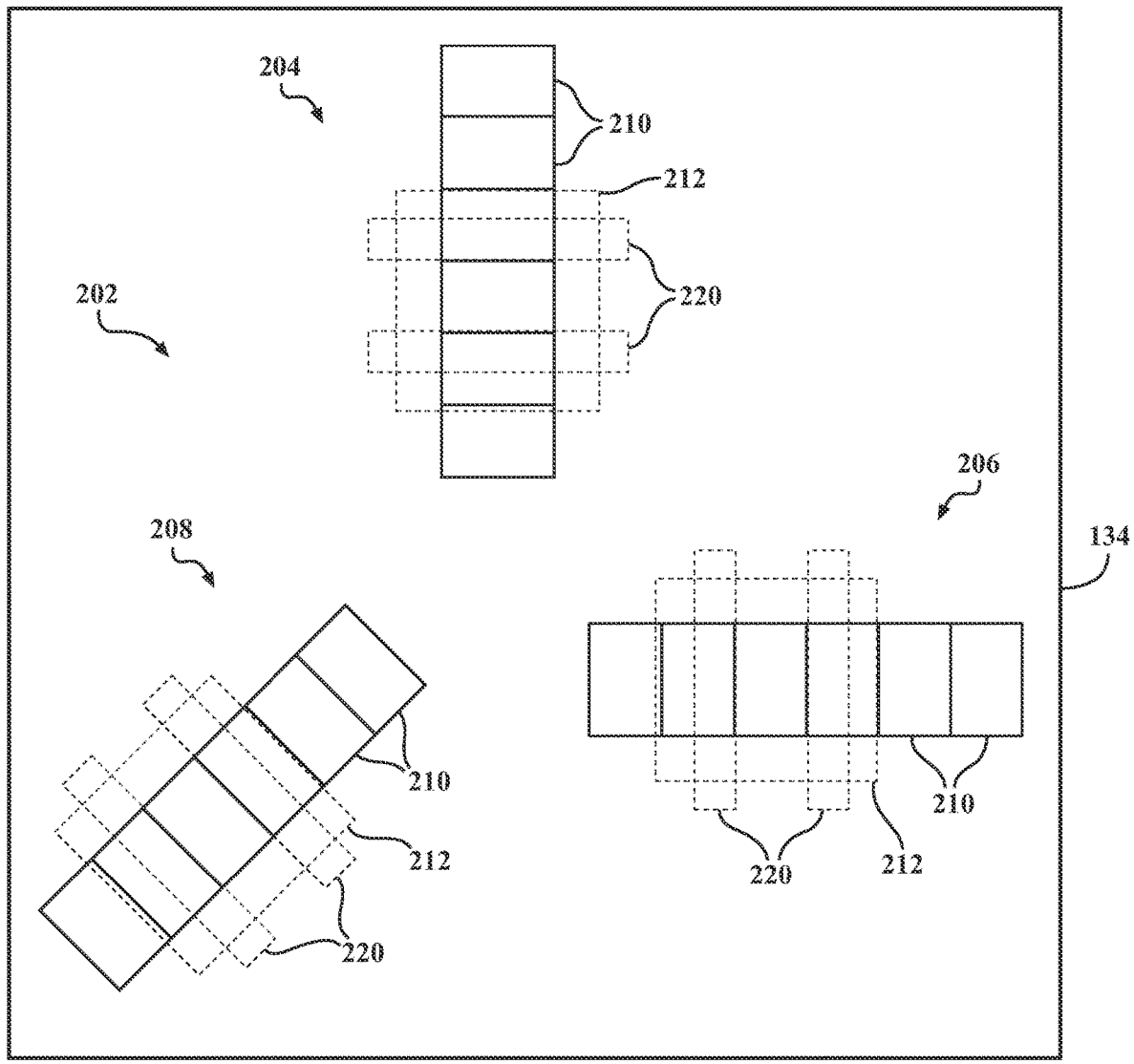
FIG. 9 is a block diagram of a camera unit that may be used with the navigation system.

Referring to FIG. 9, a block diagram of the localizer's camera unit 134 is illustrated with three of the optical sensors 140 being depicted as one-dimensional sensor arrays 202. Such sensors and their arrangement may be similar to those disclosed in U.S. Pat. No. 6,141,104, the entire contents of which are hereby incorporated herein by reference. In the illustrated embodiment, the camera unit 134 includes a first sensor array 204, a second sensor array 206, and a third sensor array 208. The first sensor array 204 may be aligned along a first axis. The second sensor array 206 may be aligned along a second axis. The third sensor array 208 may be aligned along a third axis. The camera unit 134 may include any suitable number and arrangement of sensor arrays to determine a position of a marker, such as a point light source provided by the LEDs 50. Positions may be determined using triangulation methods such as those described in U.S. Pat. Nos. 6,141,104 and 6,442,416, the entire contents of which are hereby incorporated herein by reference.

Each sensor array 202 includes a plurality of sensing elements 210. Each sensing element 210 may correspond to a pixel of a charge coupled device (CCD) or other image sensor. Each sensing element 210 may thus generate an electrical signal (hereinafter referred to as a "sensing element signal") that corresponds to an amount of light incident on that element 210. Each sensing element signal is transmitted to the camera controller 142 and/or the navigation processor 52 for processing. It should be recognized that additional image processors and/or circuits may be disposed between the sensing elements 210, the camera controller 42, and/or the navigation processor 52 for processing the sensing element signals before being transmitted to the navigation processor 52 in some embodiments.

In one embodiment, an optical filter 220 (more clearly shown in FIG. 10) may be used by the camera unit 134 to determine the position of a marker, such as a point light source provided by an LED 50. The filter 220 may include one or more apertures or slits 222 formed therein and may be positioned in front of each sensor array 202 (i.e., between each sensor array 202 and the objects within the operating room). For example, a single, straight aperture 222 may be used to focus light emitted from an LED 50 onto a line image (not shown) that is oriented substantially perpendicularly to the sensor array 202. The aperture 222 may be a long, narrow rectangular aperture within an opaque mask, for example, and may have an infinite depth of field. Accordingly, disregarding any diffraction effects, the line image may be in sharp focus regardless of the distance between the LED 50 and the sensor elements 210 of the sensor array 202. As the LED 50 moves along a path parallel to the longitudinal axis of the aperture 222, the point of intersection of the line image and the sensor array 202 remains constant. An angular field of view of the filter 220 may be changed by varying the distance between the aperture 222 and the sensor array 202.

Figure 10:
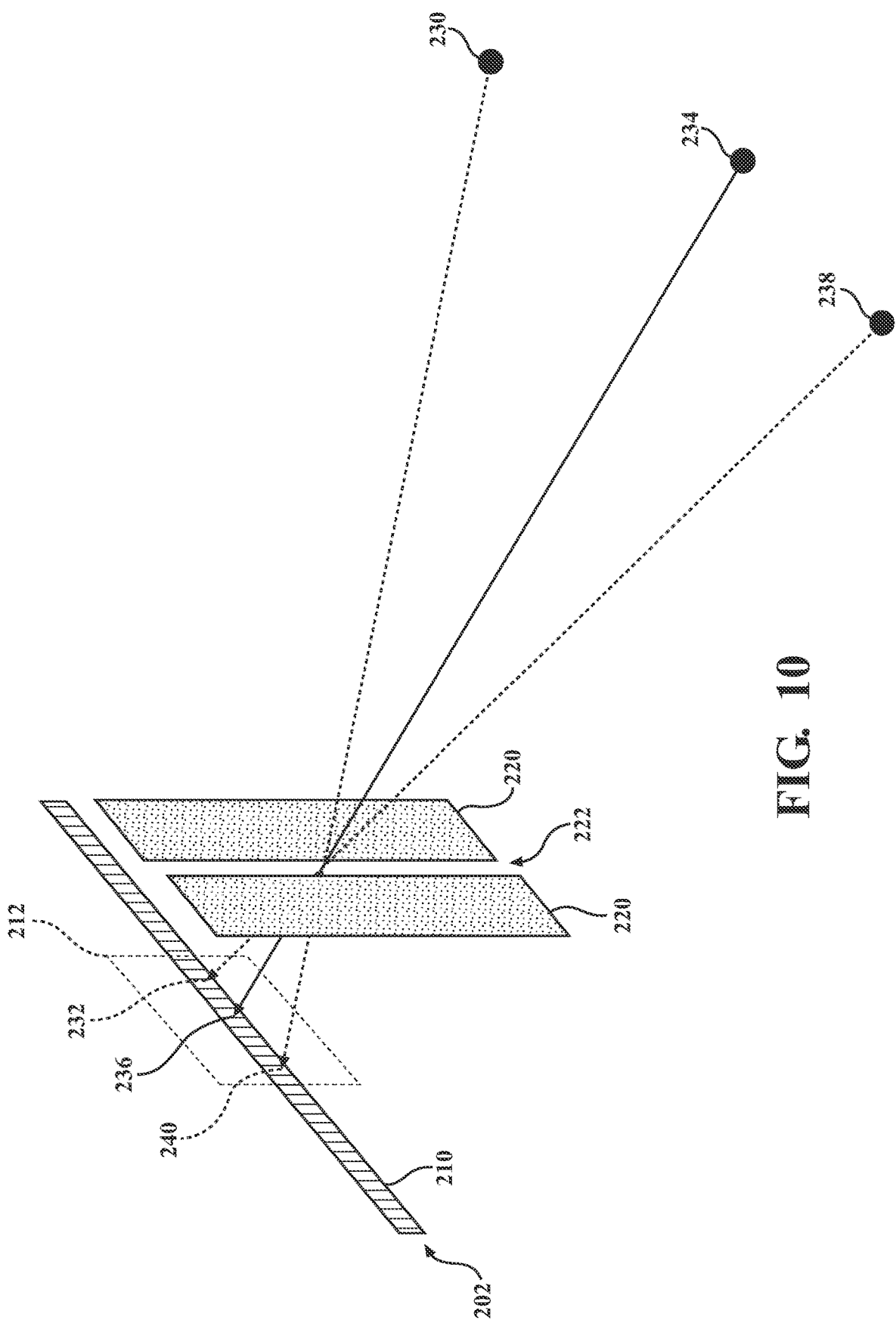
FIG. 10 is a perspective view of an optical filter that may be used to filter light received from markers within the navigation system.

Referring to FIG. 10, the point at which the line image intersects the sensor array 202 is detected by the camera controller 142. For example, the sensor element 210 or elements intersecting the line image are illuminated by the light contained within the line image, and a resulting sensor element signal is generated from each illuminated sensor element 210. The sensor element signals are received by the camera controller 142 and/or the navigation processor 52 and are used to determine the position of the LED 50. For example, in the embodiment illustrated in FIG. 10, an LED 50 in a first position 230 may cause the line image to illuminate a first sensor element 232 (or group of adjacent sensor elements). If the LED 50 moves to a second position 234, the resulting line image may illuminate a second sensor element 236 (or group of adjacent elements). Similarly, if the LED 50 moves to a third position 238, the resulting line image may illuminate a third sensor element 240 (or group of adjacent elements). The associated sensor element signals are transmitted from the illuminated sensor elements 210 to the camera controller 142 and/or navigation processor 52 to determine the associated position of the LED 50 as described above. In the event that positions 230, 234, and 238 correspond to the expected movement of an object, a resulting window (described below) for tracking the movement of the object would be defined to include sensor elements 232, 236, and 240 as well as any suitable number of adjacent sensor elements 210 corresponding to the size of the object and the expected movement of the object.

The navigation processor 52 applies a dynamic window 212 to each sensor array 202 to selectively enable and disable the processing of the sensing element signals provided by each sensor array 202. Each window 212 represents a subset of sensing elements 210 that will be processed or used by the navigation processor 52 to identify and track the location of the objects within the operating room. Accordingly, the application of the dynamic window 212 to each sensor array 202 effectively crops the usable sensing elements 210 of each sensor array 202. Thus, only the sensing elements 210 that are identified as being within the window 212 are processed by the navigation processor 52 to identify and track the pose of one or more objects within the operating room.

Each window 212 may be identified by the navigation processor 52 or the camera controller 142 based on signals that identify a location of one or more objects within the operating room, for example. In one embodiment, the camera controller 142 or the navigation processor 52 may be used to quickly identify objects of interest in the operating room as well as their general location within the room using the video camera 136. Thus, the machine vision system 12 may provide relatively low-resolution tracking of the objects within the operating room based on the machine vision information. The navigation system 20, on the other hand, may provide relatively high-resolution tracking of the objects within the operating room using the optical sensors 140.

During operation, the navigation computer 26 identifies one or more objects of interest within the operating room and determines a pose (i.e., position and/or orientation) of each object. Additionally, or alternatively, the navigation computer 26 may determine a pose of each tracker (e.g., tracker 44, 46, or 48) attached to each object of interest since each object of interest will typically include a tracker. Data representative of the identified objects and/or trackers, as well as the pose of each object and/or tracker, is transmitted from the camera controller 142 to the navigation processor 52. Since the trackers are the components that are directly tracked by the camera controller 142, rather than the objects themselves, the pose of the trackers may be used to determine which sensor elements 210 to enable or disable as described herein.

The navigation processor 52 receives, from the camera controller 142, data representative of an identification of the objects of interest that are determined by the navigation computer 26 to be present within the operating room and data representative of the pose (i.e., position and/or orientation) of each object and/or tracker within the localizer coordinate system LCLZ. The navigation processor 52 then makes a determination of what portions of each sensor array 202 to process in order to efficiently track the pose of each object and/or tracker.

For example, the navigation processor 52 may first determine which sensing elements in each sensor array 202 correspond to the present location of each object. To do so, the navigation processor 52 may reference a table or other data structure stored within memory of the navigation computer 26 or camera controller 142. The table may identify which sensing elements 210 are activated or otherwise correspond to various coordinate locations within the localizer coordinate system LCLZ. The navigation processor 52 may then identify one or more additional sensing elements 210 within each sensor array 202 that are adjacent to (i.e., on either or both sides of) the sensing elements 210 corresponding to the present position of the object. In one embodiment, the navigation processor 52 may determine the number of additional sensing elements 210 adjacent to the sensing elements 210 corresponding to the position of the object to be equal to 100% of the sensing elements 210 corresponding to the position of the object. The navigation processor 52 may then determine the window 212 for each sensor array 202 to include the sensing elements 210 corresponding to the present position of each object as well as the additional sensing elements 210 determined above. Thus, in this example, the navigation processor 52 may define the window 212 for each sensor array 202 to be equal to 3 times the number of sensing elements 210 corresponding to the size and position of the object.

It should be recognized that the navigation processor 52 may define each window 212 to include any suitable number of sensing elements 210 to enable each object to be efficiently and accurately tracked, taking into account normal or expected movement of the object. It should also be recognized that the navigation processor 52 may identify a different number of sensing elements 210 to be included within the window 212 for each sensor array 202. Accordingly, the window 212 may be defined to account for movement of the object beyond its current pose. In some cases, the window 212 may be defined to account for movement within a predetermined movement envelope (e.g., predetermined movement in any one or more of six degrees of freedom from the current pose). The expected movement may be based on prior pose data (e.g., a difference in position over time equating with a velocity and/or an acceleration of the object or tracker) in some embodiments, or may be based on the type of object being tracked.

For example, if the tracker is attached to certain portions of the anatomy (e.g., the pelvis or spine), the tracker may be expected to move a relatively small amount. If the tracker is attached to other portions of the anatomy (e.g., the tibia in a robotic knee surgery), then the surgeon may move the anatomy in a large range of motion to determine joint stability such that the tracker may be expected to move in a circular range of several inches to several feet. Accordingly, the navigation computer 26 may need to account for the current pose of each tracker and the expected range of motion of each tracker. In one embodiment, each tracker may have a unique identifier that is also detectable by the navigation computer 26. For example, each tracker may include a quick response (QR) code or other machine-readable code, or each tracker may wirelessly communicate the identifier to the navigation computer 26. Alternatively, the user may enter the identifier (e.g., tibia tracker, femur tracker, pelvis tracker, spine tracker, etc.) during an initial setup phase of the surgical procedure.

Once the current pose of each object's tracker and the likely range of movement of each object's tracker is determined, the navigation computer 26 and/or the camera controller 142 can then determine a likely field of view needed for the camera unit 134 of the navigation system 120. The windows 212 may then be based on this field of view. For example, the camera controller 142 or the navigation processor 52 may increase all windows 200% if a tibia tracker 46 is used since all windows 212 need to be able to encompass the tibia tracker 46. However, if all trackers are unlikely to move a large amount, then the windows 212 can be set to a smaller size. As a result, the camera controller 142 or the navigation processor 52 may dynamically update the windows 212 based on the type of tracker or object being tracked, the expected movement of the object or tracker, and/or based on the prior pose data (e.g., velocity and/or acceleration) of the object or tracker.

It should be recognized that each window 212 may be different for each sensor array 202. Thus, in one embodiment, the window 212 for the first sensor array 204 may include a first number of sensing elements 210 corresponding to the position of the objects, the second sensor array 206 may include a different, second number of sensing elements 210 corresponding to the position of the objects, and the third sensor array 208 may include a different, third number of sensing elements 210 corresponding to the position of the objects.

As described herein, the processing of only a subset of sensing elements 210 from each sensor array 202 enables a processing load to be reduced when the navigation processor 52 processes the sensing element signals to track the position of the objects within the operating room. As a result, the localizer 34 may sample the light signals received from the trackers 44, 46, 48 at a higher frequency than the localizer 34 might otherwise be able to sample if the navigation processor 52 was configured to process all sensing element signals from all sensing elements 210.

While the embodiments herein are described as being performed by the navigation processor 52, it should be recognized that the identification and determination of the windows 212 and the subsets of sensing elements 210 included within and adjacent to the windows 212 may be additionally or alternatively performed by the camera controller 142 or another suitable processor or controller.

Referring to FIG. 11, in one embodiment, each dynamic window 212 may be implemented using an array 302 of bit masks 304. Each bit mask 304 of the bit mask array 302 corresponds to sensing element data 306 output by an individual sensing element 210 of an individual sensor array 202. Thus, each bit mask 304 of the bit mask array 302 may cause the navigation processor 52 to make a decision to enable or disable the processing of data from a respective sensing element 210. For example, if the navigation processor 52 (or another processor) stores a bit value of 1 in the bit mask 304, the navigation processor 52 may enable the processing of the data from the associated sensing element 210. Similarly, storing a bit value of 0 may disable the processing of the data from the associated sensing element 210. The bit mask array 302 for each sensor array 202 may be stored in the memory of the navigation computer 26 as one or more data structures.

Referring to FIG. 12, in an alternative embodiment, the bit masks may be implemented in hardware as an array 402 of transistors or other gating devices 404 that selectively enable or disable each sensing element signal from reaching the navigation processor 52. Thus, each gating device 404 may be controlled by the navigation processor 52 (or another processor such as the camera controller 142) to enable or prevent the sensing element data from being processed by the navigation processor 52. For example, if the navigation processor 52 (or another processor) activates the gating device (i.e., by enabling the gating device to conduct), the gating device 404 may enable the data from the associated sensing element 210 to be transmitted to the navigation processor 52. Similarly, deactivating the gating device 404 may prevent the data from the associated sensing element 210 from being transmitted to the navigation processor 52. The gating devices 404 may be positioned within the camera unit 36 or another suitable portion of the navigation system 20 in an electrical path between the sensing elements 210 and the navigation processor 52.

Figure 13:
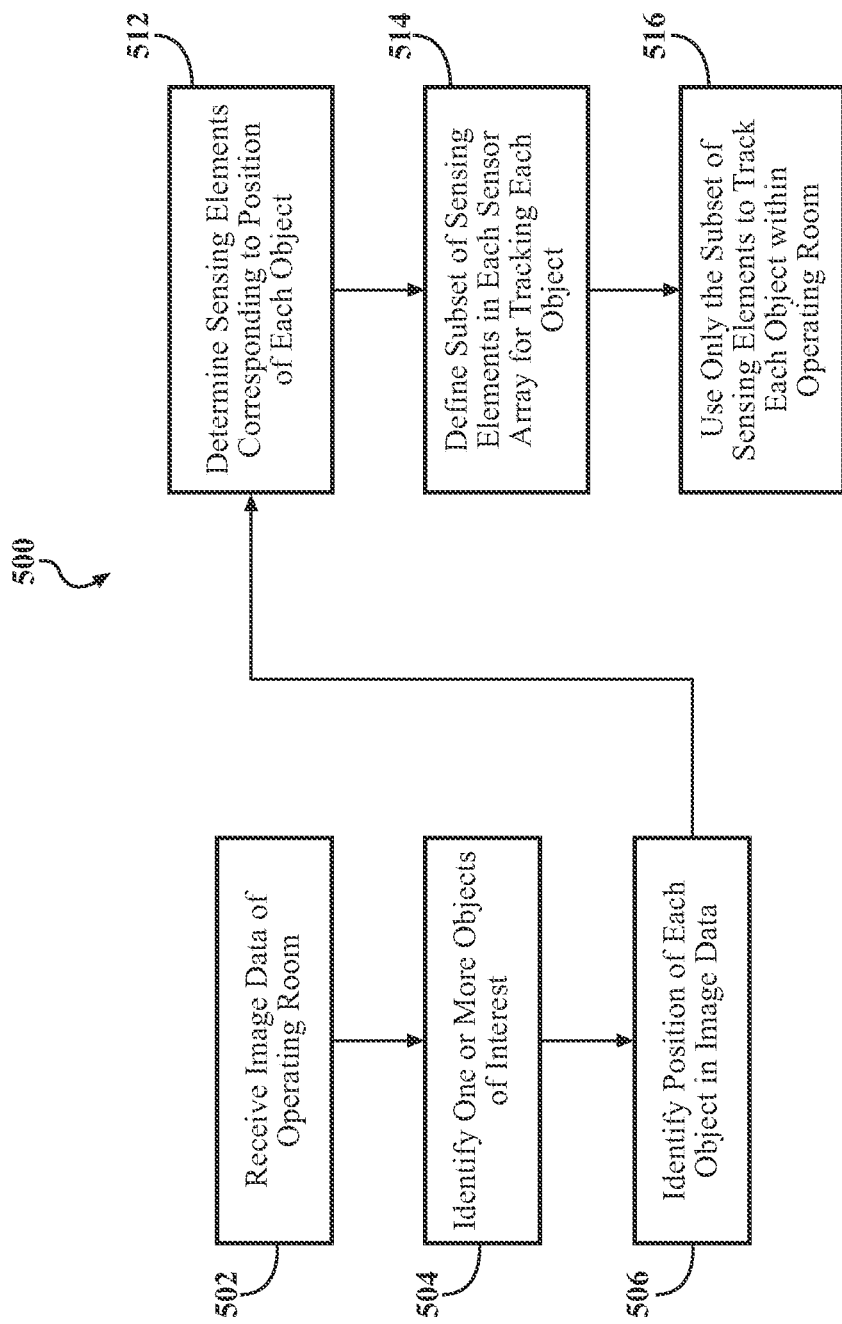
FIG. 13 is a flow diagram of a method of tracking objects within an operating room.

FIG. 13 is a flow diagram of a method 500 for tracking objects within an operating room. For example, the method 500 may be used to track surgical instruments 22 and other tools that a surgeon may use to operate on a patient, as well as tracking the patient's anatomy. The method includes receiving image data of the operating room. The method includes identifying one or more objects of interest in the operating room. The method includes identifying the position of each object of interest in the image data. The method includes determining the sensing elements corresponding to the identified position of each object. The method includes defining a subset of sensing elements in each sensor used for tracking each object of interest. The method includes using only the subset of sensing elements to track the object within the operating room.

In an embodiment, each step of the method 500 may be implemented as one or more computer-executable instructions that are stored within one or more computer-readable media. In a specific embodiment, the method 500 may be implemented using the navigation system 20 shown in FIG. 1, or the navigation system 120 shown in FIG. 8. For example, the camera controller 42, 142, and/or the navigation processor 52 may execute instructions stored within memory of the camera controller 42, 142 and/or the navigation system 20 to perform the steps of the method 500 described herein.

In one embodiment, the method 500 includes receiving 502 image data of the operating room from one or more optical sensors 40 or machine vision camera 36. For example, in a partial or total knee replacement surgery, the optical sensors 40 or machine vision camera 36 may generate image data of the surgeon, the patient, the trackers 46, 48 attached to the patient's femur F and tibia T, respectively, the surgical instrument 22, and the tool tracker 48, among others. The method includes identifying 504 one or more objects of interest from the image data. The objects of interest may be defined in a similar manner as described above with reference to disclosed embodiments. In the example of a knee replacement surgery, the objects of interest may include the surgical instrument 22, the femur F, the tibia T, and the trackers 44, 46, 48. In one embodiment, identifying each tracker 44, 46, 48 includes using an identifier unique to that tracker as described above. The method may also identify 506 a position of each object in the image data as described above.

The method may also determine an expected movement or change in pose of each object in a similar manner as described above. For example, the method may use a lookup table or another suitable data structure stored in memory to correlate the type of object with an expected range of motion or change in pose. Additionally, or alternatively, the method may reference prior pose data of each object to determine a velocity, acceleration, and/or expected change in pose of each object. The method may then determine the expected movement or change in pose of each object.

The navigation processor 52 may also determine 512 which sensor elements of optical sensor 40 or sensing elements 210 of each sensor array 202, within the camera unit 36, 134 correspond to the location of each object within the localizer coordinate system LCLZ.

The navigation processor 52 may then determine 514 a subset of sensor elements of optical sensor 40 or sensing elements 210 within each sensor array 202 that will be used to track each object. For example, the navigation processor 52 may determine each region of interest 76 or subset of sensing elements 210 to include the additional elements determined in step 512 as well as a predetermined number of elements determined in step 512. These elements may be defined as being included in a region of interest 76 or window 212 that may be dynamically updated based on new data received and/or new data determined by the navigation processor 52. As noted above, the region of interest 76 or windows 212 may be dynamically updated to include the elements corresponding to the expected movement or change of pose of each object. When the navigation processor 52 has determined each subset of elements in step 514, the navigation processor 52 uses 516 only the subset of elements to track each identified object within the operating room. In one embodiment, the navigation processor 26 and/or the camera controller 42, 142 only reads out information from sensor elements within the region of interest 76 or window 212. In one embodiment, the navigation processor 52 uses a bit mask array 302 such as described in FIG. 6 or an array 402 of gating devices such as described in FIG. 7 to process only the subset of sensing elements 210. Alternatively, the navigation processor 52 may use any suitable device or technique to process only the selected subset of elements for tracking the objects.

Accordingly, as described herein, the method may be used to identify each object of interest within a space, such as an operating room. The navigation system 20, including the localizer 34 and camera unit 36, 134 provide high speed, high fidelity tracking of the objects. The navigation system 20 may accomplish this by only activating the elements within one or more dynamically defined regions of interest 76 or windows 212 corresponding to the position and/or expected movement of each object while deactivating the elements that are not included within the region of interest 76 or windows 212. As a result, the navigation processor 52 and/or the camera controller 42, 142 may benefit from a reduced processing workload resulting from the reduced number of sensor element signals needing to be processed to track the objects.

Several embodiments have been discussed in the foregoing description. However, the embodiments discussed herein are not intended to be exhaustive or limit the invention to any particular form. The terminology that has been used is intended to be in the nature of words of description rather than of limitation. Many modifications and variations are possible in light of the above teachings and the invention may be practiced otherwise than as specifically described.

What is claimed is:

1. A surgical navigation system for tracking an object within an operating room, the surgical navigation system comprising:
    a camera unit comprising:
        a housing;
        a first optical sensor coupled to housing and comprising sensing elements adapted to sense light in a near-infrared spectrum;
        a second optical sensor coupled to the housing and being adapted to sense light in a visible light spectrum; and
    a controller in communication with the first and second optical sensors, and wherein the controller is configured to:
        obtain, from the second optical sensor, data related to the object within the operating room; and
        modify control of the sensing elements of the first optical sensor based on the data of the object obtained by the second optical sensor.

2. The surgical navigation system of claim 1, wherein the data related to the object within the operating room comprises one or more of (1) a type of the object (2) a pose data of the object, and/or (3) an expected movement of the object.

3. The surgical navigation system of claim 2, wherein the controller is configured to modify control of the sensing elements to activate a subset of the sensing elements, the subset being less than all of the sensing elements.

4. The surgical navigation system of claim 2, wherein the controller is configured to modify control of the sensing elements to prevent processing of a subset of the sensing elements, the subset being less than all of the sensing elements.

5. The surgical navigation system of claim 2, wherein the controller is configured to modify control of the sensing elements to adjust a size of a field-of-view viewed by the first optical sensor.

6. The surgical navigation system of claim 2, wherein the controller is configured to modify control of the sensing elements to define a size and/or position of a region-of-interest viewed by the first optical sensor, the region-of-interest being a sub-region within a full field-of-view of the first optical sensor.

7. The surgical navigation system of claim 2, wherein the controller is configured to modify control of the sensing elements by adjusting a frequency by which the sensing elements are read-out.

8. The surgical navigation system of claim 2, wherein the pose data of the object includes one or more of: a velocity of the object and/or an acceleration of the object.

9. The surgical navigation system of claim 1, wherein the camera unit comprises two first optical sensors coupled to the housing and each comprising the sensing elements adapted to sense light in the near-infrared spectrum.

10. The surgical navigation system of claim 9, wherein the camera unit comprises:
    a rigid support structure disposed within the housing and being configured to support the two first optical sensors, and wherein the two first optical sensors are spaced apart from one another on the rigid support structure; and
    the second optical sensor rigidly supported by the housing relative to the two first optical sensors in a predefined relationship.

11. The surgical navigation system of claim 9, wherein the housing has an elongated shape defining a first end and an opposing second end, and wherein one of the first optical sensors is disposed adjacent to the first end of the housing and the other one of the first optical sensors is disposed adjacent to the opposing second end of the housing.

12. A method of operating a surgical navigation system for tracking an object within an operating room, the surgical navigation system comprising a camera unit comprising a housing, a first optical sensor coupled to housing and comprising sensing elements adapted to sense light in a near-infrared spectrum, a second optical sensor coupled to the housing and being adapted to sense light in a visible light spectrum, and a controller in communication with the first and second optical sensors, the method comprising the controller performing the steps of:
    obtaining, from the second optical sensor, data related to the object within the operating room; and
    modifying control of the sensing elements of the first optical sensor based on the data of the object obtained by the second optical sensor.

13. The method of claim 12, comprising the controller obtaining the data related to the object as being one or more of: (1) a type of the object (2) a pose data of the object, and/or (3) an expected movement of the object.

14. The method of claim 13, comprising the controller modifying control of the sensing elements by activating a subset of the sensing elements, the subset being less than all of the sensing elements.

15. The method of claim 13, comprising the controller modifying control of the sensing elements by preventing processing of a subset of the sensing elements, the subset being less than all of the sensing elements.

16. The method of claim 13, comprising the controller modifying control of the sensing elements for adjusting a size of a field-of-view viewed by the first optical sensor.

17. The method of claim 13, comprising the controller modifying control of the sensing elements for defining a size and/or position of a region-of-interest viewed by the first optical sensor, the region-of-interest being a sub-region within a full field-of-view of the first optical sensor.

18. The method of claim 13, comprising the controller modifying control of the sensing elements by adjusting a frequency by which the sensing elements are read-out.

19. The method of claim 13, comprising the controller obtaining the pose data of the object as being one or more of: a velocity of the object and/or an acceleration of the object.

20. A camera unit for tracking an object within an operating room, the camera unit comprising:
- a first optical sensor comprising sensing elements adapted to sense light in a near-infrared spectrum;
- a second optical sensor adapted to sense light in a visible light spectrum; and
- a controller in communication with the first and second optical sensors, and wherein the controller is configured to:
  - obtain, from the second optical sensor, data related to the object within the operating room; and
  - modify control of the sensing elements of the first optical sensor based on the data of the object obtained by the second optical sensor.

* * * * *